US008496625B2

(12) United States Patent
Brugger et al.

(10) Patent No.: US 8,496,625 B2
(45) Date of Patent: Jul. 30, 2013

(54) SAFE NEEDLE METHODS, APPARATUS, AND SYSTEMS

(75) Inventors: James M. Brugger, Newburyport, MA (US); Steven C. Alford, Marysville, WA (US); William Schnell, Libertyville, IL (US); Mark Florence, Shrewsbury, MA (US)

(73) Assignee: NxStage Medical, Inc., Lawrence, MA (US)

( * ) Notice: Subject to any disclaimer, the term of this patent is extended or adjusted under 35 U.S.C. 154(b) by 147 days.

(21) Appl. No.: 13/116,597

(22) Filed: May 26, 2011

(65) Prior Publication Data

US 2011/0295207 A1 Dec. 1, 2011

Related U.S. Application Data

(60) Provisional application No. 61/348,695, filed on May 26, 2010, provisional application No. 61/354,645, filed on Jun. 14, 2010.

(51) Int. Cl.
*A61M 5/32* (2006.01)

(52) U.S. Cl.
USPC ............... 604/177; 604/180; 602/41; 602/52

(58) Field of Classification Search
USPC ............ 604/164.01, 164.04, 174, 177–180, 604/304, 307; 602/41, 48, 52, 54; 128/DIG. 6
See application file for complete search history.

(56) References Cited

U.S. PATENT DOCUMENTS

| | | | | |
|---|---|---|---|---|
| 5,087,248 | A * | 2/1992 | Beisang, III | 604/180 |
| 7,591,804 | B2 * | 9/2009 | Utterberg et al. | 604/177 |
| 7,618,400 | B2 | 11/2009 | Chawki | |
| 8,157,770 | B2 * | 4/2012 | Elwell et al. | 604/180 |
| 2007/0265571 | A1 | 11/2007 | Utterberg et al. | |
| 2010/0076362 | A1 | 3/2010 | Utterberg et al. | |
| 2012/0109070 | A1 * | 5/2012 | Elsamahy et al. | 604/179 |

OTHER PUBLICATIONS

Medisystems AV Fistula Needle Set with MasterGuard Anti-Stick Needle Protector—Instruction sheet [online], [retrieved on Aug. 15, 2011]. Retrieved from the Internet: <URL: http://www.medisystems.com/NC45-0102.pdf>.
Medisystems AV Fistula Needle Set with MasterGuard Anti-Stick Needle Protector—Reference Sheet [online], [retrieved on Aug. 15, 2011]. Retrieved from the Internet: <URL: http://www.medisystems.com/documents/TM0414.pdf>.
Medisystems AV Fistula Needles with MasterGuard Anti-Stick Needle Protector—Brochure [online], [retrieved on Aug. 15, 2011]. Retrieved from the Internet: <URL: http://www.medisystems.com/documents/APM304_MasterGuardBrochure.pdf>.

* cited by examiner

*Primary Examiner* — Theodore Stigell
(74) *Attorney, Agent, or Firm* — Miles & Stockbridge, P.C.; Mark A. Catan

(57) ABSTRACT

A bandage can be used to secure a needle to an access site so as to prevent unintended movement or withdrawal of the needle from the access site during administration of a treatment to a patient. After treatment, the needle can be removed by manipulating a portion of the bandage. Another portion of the bandage can be maintained in position over the access site during needle removal and can be used to promote clotting of the site after needle removal. The bandage may include a clotting agent, a hemostasis pad, and/or a clot-promoting structure. Additionally or alternatively, finger pressure can be applied to the access site through the bandage. For example, the bandage may include a viewing window without any adhesive to allow visual monitoring of the access site during treatment. Finger pressure may be applied to the viewing window and thereby to the access site during and after needle removal to encourage hemostasis.

20 Claims, 24 Drawing Sheets

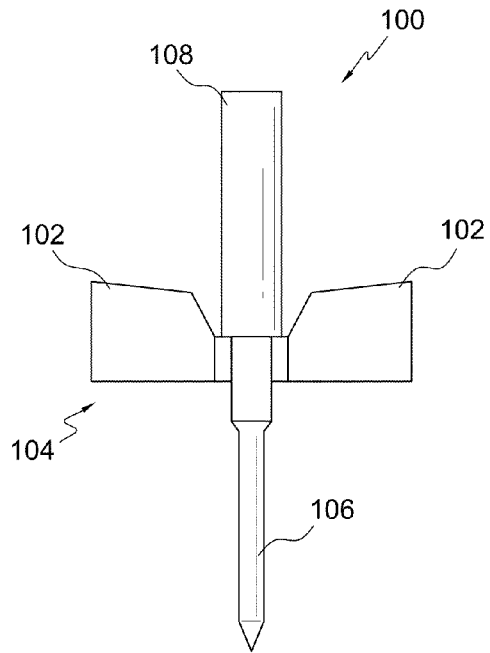
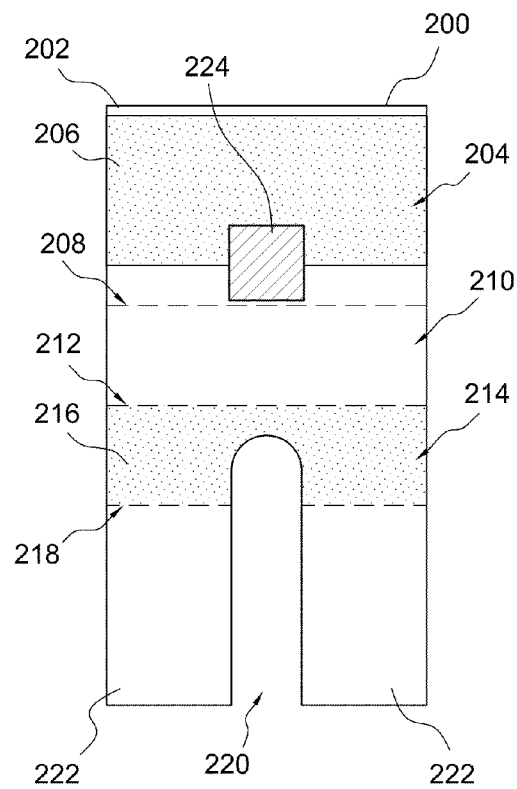
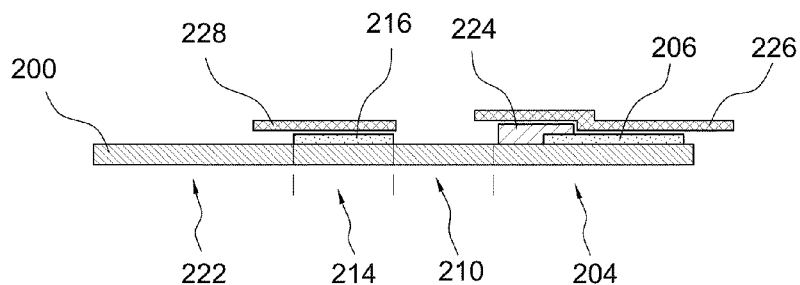
FIG. 1
FIG. 2A
FIG. 2B

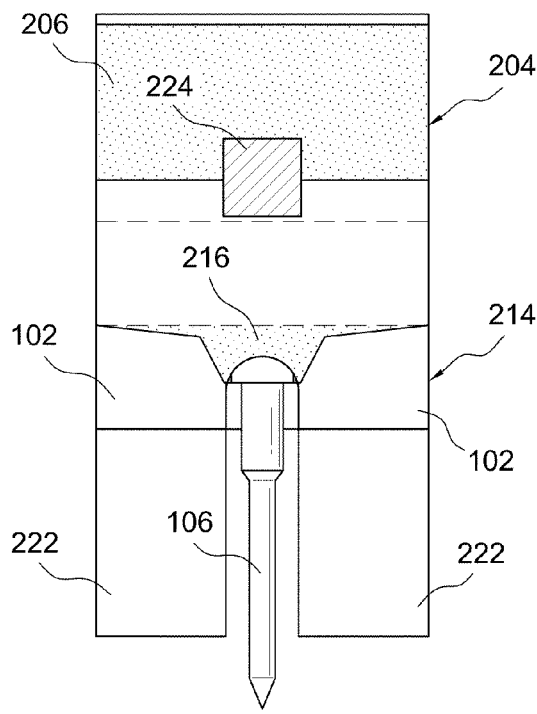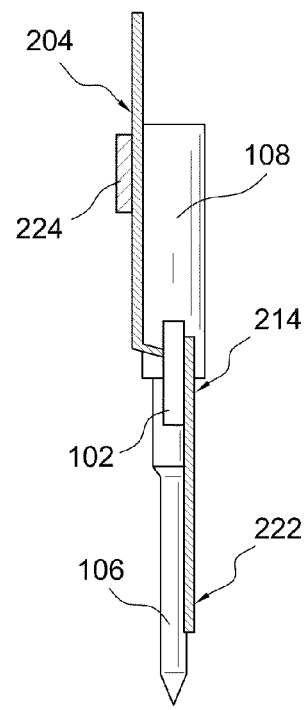
FIG. 3A  FIG. 3B
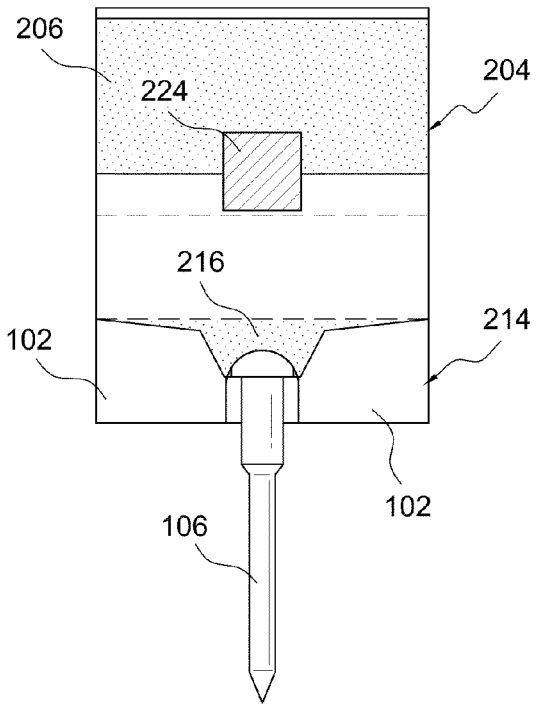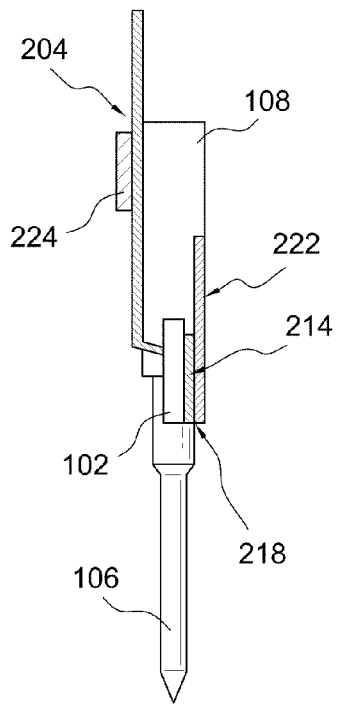
FIG. 3C  FIG. 3D

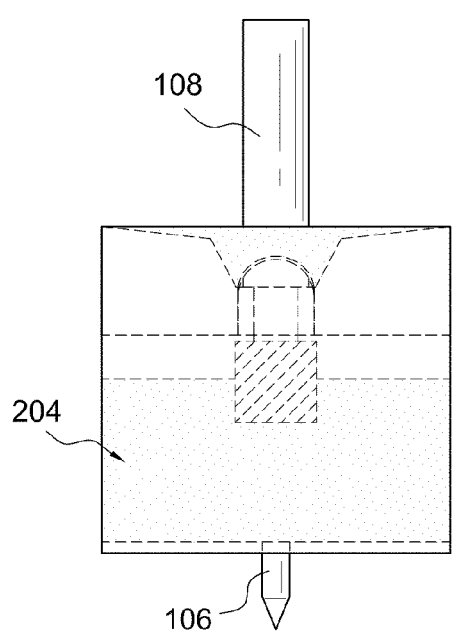
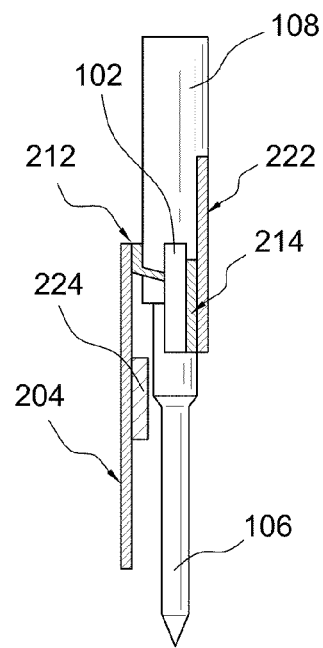
FIG. 3E  FIG. 3F
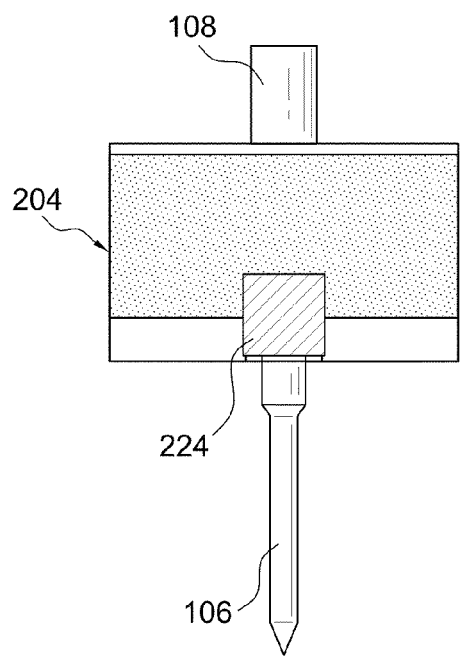
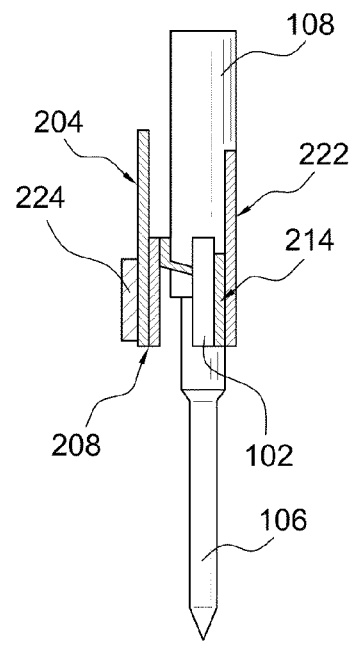
FIG. 3G  FIG. 3H

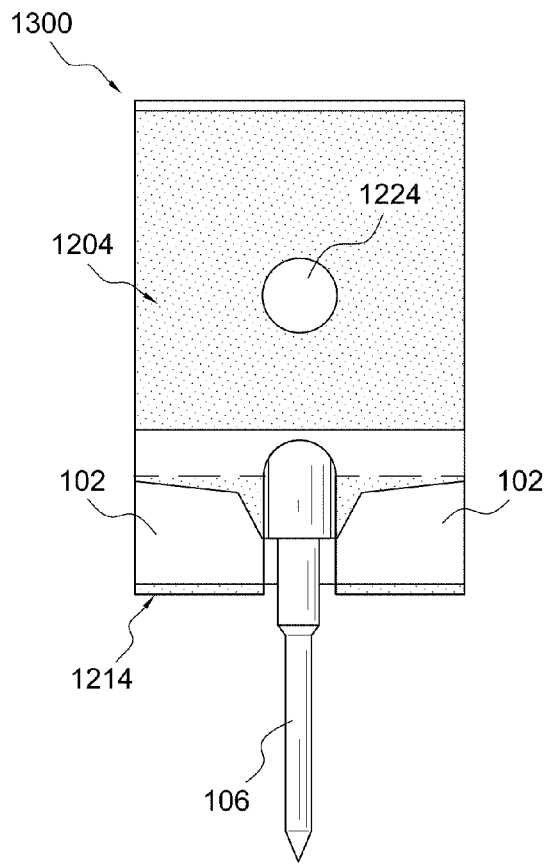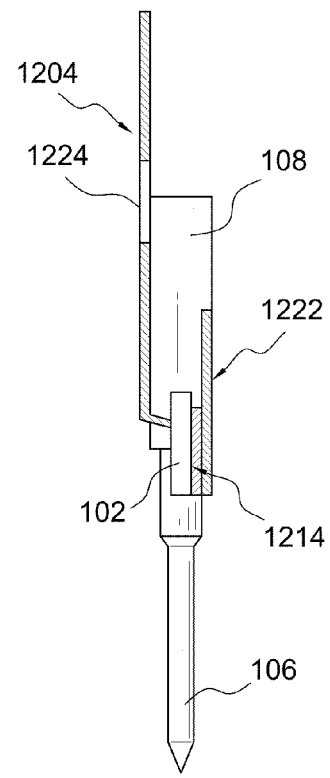
FIG. 13A  FIG. 13B
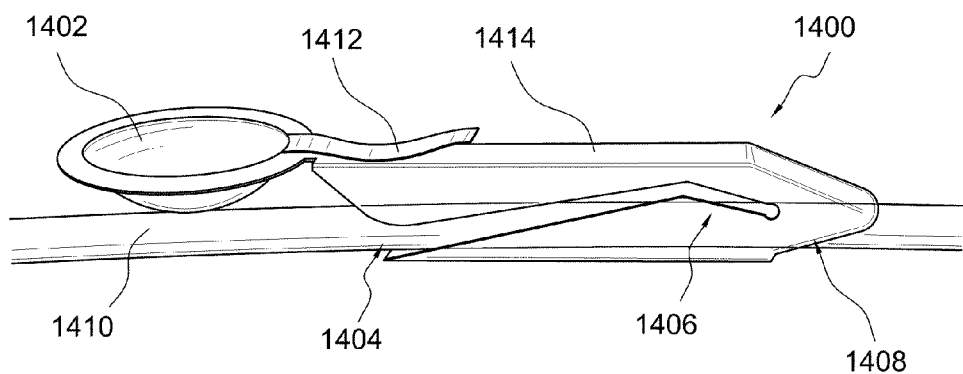
FIG. 14

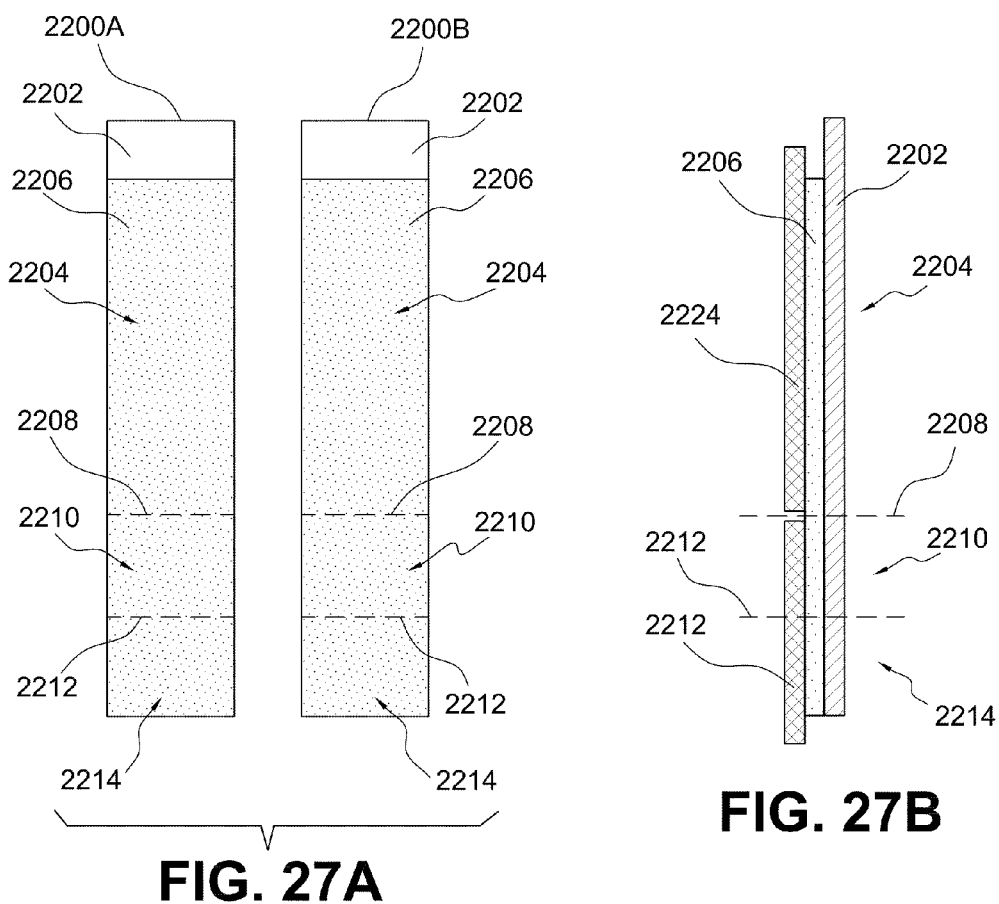
FIG. 27A
FIG. 27B
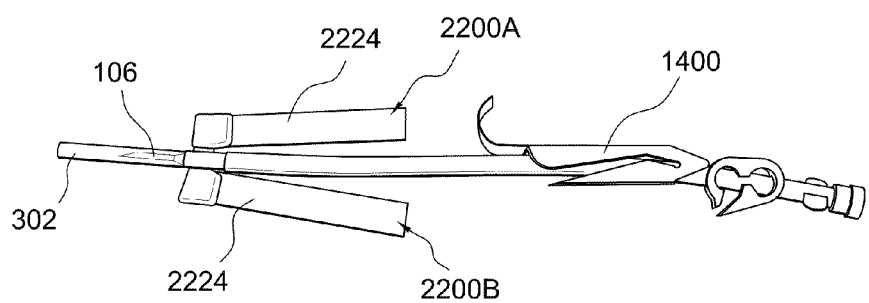
FIG. 28

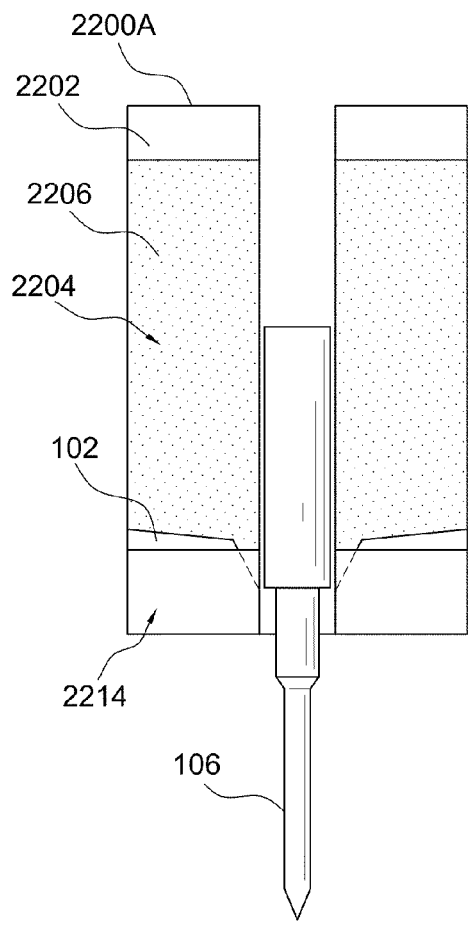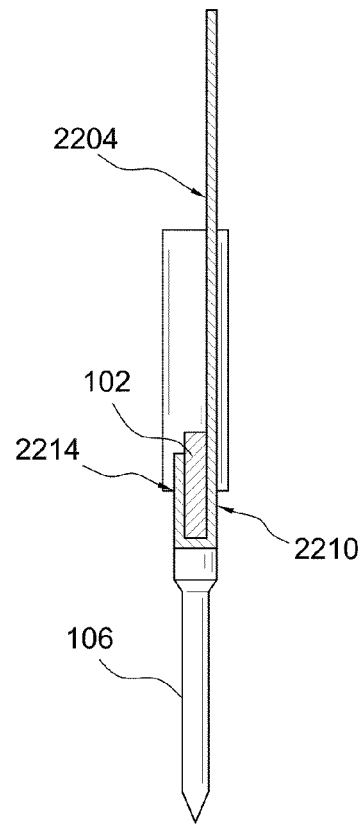
FIG. 29A    FIG. 29B
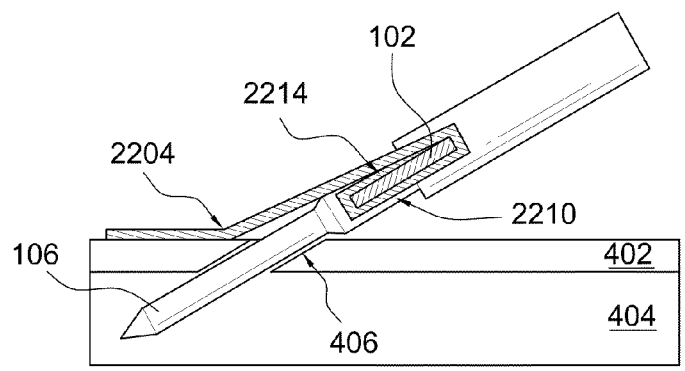
FIG. 30

SAFE NEEDLE METHODS, APPARATUS, AND SYSTEMS

CROSS-REFERENCE TO RELATED APPLICATIONS

The present application claims the benefit of U.S. Provisional Application No. 61/348,695, filed May 26, 2010, and U.S. Provisional Application No. 61/354,645, filed Jun. 14, 2010, both of which are hereby incorporated by reference herein in there entireties.

FIELD

The present disclosure relates generally to needles for intravenous or subcutaneous insertion into a patient, and, more particularly, to safety methods, apparatuses, and systems for securing and protecting a needle inserted into an access site of the patient. The present disclosure also relates to bandages and methods for using bandages to secure a needle when inserted into an access site of a patient and to promote clotting after removal of the needle from the access site.

SUMMARY

A bandage of flexible material can resist extraction of a needle, such as a butterfly needle, when it has been inserted into a patient access site. A first portion of the bandage can be releasably attached to wings of the butterfly needle. A second portion of the bandage includes an adhesive that holds the needle to the skin. When attached to the needle, the arrangement of the first and second portions of the bandage prevents the needle from moving away from the access site when the bandage is applied to the patient. The first portion may be attached to the back-side of wings of the needle hub with the bandage looping over the front-side of the wings and extending to the second portion, which is attached to the skin of the patient. Once treatment is completed, the first portion may be released from the wings by pulling on an end portion of the bandage adjacent to the first portion. After the first portion is released, the bandage is no longer attached to the butterfly needle such that the needle can be removed from the access site while the second portion of the bandage remains in place. The bandage can include a hemostasis pad over the access site to encourage clotting after needle removal. Alternatively or additionally, the bandage can include a viewing window over the access site to allow for viewing of the access site during treatment.

Looping a portion of the bandage over the front side of the wings to secure the needle to the access site can also be achieved using different bandage configurations. For example, the bandage may be configured as two strips of medical tape. A portion of the tape can be adhered to the back-side of the wings of the needle with the remaining portion of the tape extending away from the needle tip and the access site. The remaining portions of the tape can be looped back over the front-side of the wings (toward the needle tip and access site) and adhered to portions of the skin adjacent to or at least proximal to the access site.

In some embodiments, a needle securing device can be used to secure the needle in the patient access site. The bandage and/or tape can be applied to the securing device to attach it to the patient's skin in a secure manner. For example, the bandage can be configured as two strips of medical tape. When the securing device is a wedge-shaped securing device, a portion of the tape can be adhered to the skin-adjacent-side of the securing device with the remaining portion of the tape extending away from the needle tip and the access site. The remaining portions of the tape can be looped back over the top-side of the securing device as well as the front-side of the wings (toward the needle tip and access site). This remaining portion can then be adhered to portions of the skin adjacent to or at least proximate to the access site to secure both the securing device and the needle to the patient.

In addition, aspects of the disclosed subject matter may be applied to securing needles to a patient access site with a bandage and to allowing removal of the needle by manipulating the bandage. Clotting of the patient access site can be encouraged by applying pressure through the bandage to the patient access site. For example, a first portion of the bandage can include a viewing window that is positioned over the patient access site. The viewing window can be provided without any adhesive, but can be surrounded by a region with adhesive thereon. Alternatively or additionally, the window can include a clot promoting component, such as, but not limited to, a clotting agent, a hemostasis pad, and a protruding bubble portion filled with air. A second portion of the bandage can secure the needle to the skin of the patient during use of the needle, for example, to effect a treatment. After treatment, the second portion may be disengaged from the skin to allow removal of the needle from the patient access site. Finger pressure can be applied to the viewing window during needle removal, after which at least the adhesive region of the first portion is secured to the patient skin while pressure is maintained to promote hemostasis.

In embodiments, a bandage can secure a butterfly needle to a patient access site. The needle can have a pair of wings extending radially from the hub of the needle. The bandage can be a flexible material having a first region, a second region, and a third region. The first region can have a first adhesive on at least a surface portion thereof. The second region can have a gap therein so as to form a pair of tabs separated by the gap. The tabs may be free from any adhesive. The third region can be arranged between the first and second regions and can have a second adhesive on at least a surface portion thereof. The bandage can further include a hemostasis pad arranged in the first region. The hemostasis pad may be constructed to promote clotting of blood that contacts said pad. The third region can be arranged so as to contact the pair of wings of the butterfly needle for releasably coupling the bandage thereto. The hemostasis pad can be arranged so as to contact the patient access site when the third region is coupled to the butterfly needle.

In embodiments, a needle assembly can include a butterfly needle having a tip, a hub with a pair of wings extending radially therefrom, and tubing extending from the hub and in fluid communication with the tip. The needle assembly may further include a bandage for securing the butterfly needle to a patient access site when the needle is inserted therein. The bandage can have a first end region, a second end region, and a middle region between the first and second end regions. The first end region can have a first adhesive on at least a portion thereof and a hemostasis pad. The second end region can be without any adhesive. The middle region can be releasably connected to the pair of wings by a second adhesive on at least a portion of the middle region. The first end region can be arranged so as to releasably connect to a patient's skin with the hemostasis pad adjacent to a patient access site when the butterfly needle is inserted into the patient access site.

In embodiments, a kit for connecting to a patient access can include a butterfly needle and a bandage. The butterfly needle can include a tip, a hub with a pair of wings extending radially therefrom, and tubing extending from the hub and in fluid communication with the tip. The bandage can be a flexible material having a first region, a second region, and a third region. The first region can have a first adhesive on at least a surface portion thereof. The second region can have a gap therein so as to form a pair of tabs separated by the gap. The tabs may be free from any adhesive. The third region can be arranged between the first and second regions and can have a second adhesive on at least a surface portion thereof. The bandage can further include a hemostasis pad arranged in the first region. The hemostasis pad may be constructed to promote clotting of blood that contacts said pad. The third region can be arranged so as to contact the pair of wings of the butterfly needle for releasably coupling the bandage thereto. The hemostasis pad can be arranged so as to contact the patient access site when the third region is coupled to the butterfly needle.

In embodiments, a bandage can secure a butterfly needle to a patient access site. The needle can have a pair of wings extending radially from the hub of the needle. The bandage can be a flexible material having a first region, a second region, and a third region. The first region can have a first adhesive on at least a surface portion thereof and a window. The window in the first region can be transparent and without any adhesive thereon. The second region can have a gap therein so as to form a pair of tabs separated by the gap. The tabs can be free from any adhesive. The third region can be arranged between the first and second regions and can have a second adhesive on at least a surface portion thereof. The third region can be arranged so as to contact the pair of wings of the butterfly needle for releasably coupling the bandage thereto. The window can be arranged so as to be located over the patient access site when the third region is coupled to the butterfly needle inserted into said access site.

In embodiments, a method for connecting to a patient access site with a butterfly needle can include affixing a bandage to wings of the butterfly needle. The butterfly needle can include a tip, a hub with a pair of wings extending radially therefrom, and tubing extending from the hub and in fluid communication with the tip. The bandage can be a flexible material having a first region, a second region, and a third region. The first region can have a first adhesive on at least a surface portion thereof. The second region can have a gap therein so as to form a pair of tabs separated by the gap. The tabs may be free from any adhesive. The third region can be arranged between the first and second regions and can have a second adhesive on at least a surface portion thereof. The bandage can further include a hemostasis pad arranged in the first region. The hemostasis pad may be constructed to promote clotting of blood that contacts said pad. The third region can be affixed to the pair of wings of the butterfly needle for releasably coupling the bandage thereto. The hemostasis pad can be arranged so as to contact the patient access site when the third region is coupled to the butterfly needle.

The method can further include inserting the tip of the butterfly needle into the patient access site and affixing the first region onto skin of the patient proximal to the patient access site. The method can also include, after the inserting, removing the third region of the bandage from the wings of the butterfly needle. The method can further include removing the tip of the butterfly needle from the patient access site while contacting the hemostasis pad with the patient access site.

In embodiments, a method for connecting to a patient access site with a butterfly needle can include affixing a bandage to wings of the butterfly needle. The butterfly needle can include a tip, a hub with a pair of wings extending radially therefrom, and tubing extending from the hub and in fluid communication with the tip. The bandage can be a flexible material having a first region, a second region, and a third region. The first region can have a first adhesive on at least a surface portion thereof and a window. The window in the first region can be transparent and without any adhesive thereon. The second region can have a gap therein so as to form a pair of tabs separated by the gap. The tabs can be free from any adhesive. The third region can be arranged between the first and second regions and can have a second adhesive on at least a surface portion thereof. The third region can be affixed to the pair of wings of the butterfly needle for releasably coupling the bandage thereto. The window can be arranged so as to be located over the patient access site when the third region is coupled to the butterfly needle inserted into said access site.

The method can further include inserting the tip of the butterfly needle into the patient access site and affixing the first region onto skin of the patient such that the window overlays the patient access site. The method can also include, after the inserting, removing the third region of the bandage from the wings of the butterfly needle. The method can also include removing the tip of the butterfly needle from the patient access site while said first region of the bandage remains affixed to the skin.

In embodiments, a bandage can secure a butterfly needle to a patient access site. The needle can have a pair of wings extending radially from the hub of the needle. The bandage can be a pair of strips of flexible material. Each strip can have a first region, a second region, and a third region. The first region can have an adhesive on at least a surface portion thereof. The second region can also have an adhesive on at least a surface portion thereof. The second region can be arranged so as to contact a front surface of the one of the pair of wings of the butterfly needle. The third region can be arranged between the first and second regions and to contact a back surface of one of the pair of wings of the butterfly needle. The first region can be arranged so as to contact skin adjacent the patient access site when the second and third regions are coupled to the respective surfaces of the pair of wings of the butterfly needle inserted into the patient access site.

In embodiments, a securing device for a butterfly needle can include a wedge-shaped securing device and a bandage. The butterfly needle can have a tip, a hub with a pair of wings extending radially therefrom, and tubing extending from the hub and in fluid communication with the tip. The wedge-shaped securing device can have a first surface arranged so as to be adjacent to skin of a patient and a second surface inclined with respect to the first surface. The second surface can be arranged to contact a back surface of said pair of wings. The bandage can have a pair of flexible strips. Each strip can have an adhesive first portion, an adhesive second portion, and a middle portion between the first and second portions. The middle portion can be in contact with the first surface of the securing device such that the middle portion is between the first surface and the patient skin. The second portion can adhere to the second surface of the securing device. The first portion can be arranged so as to contact and adhere to the patient skin adjacent a patient access when the butterfly needle is inserted into the patient access and the second surface is in contact with the back surface of the pair of wings.

In embodiments, a method for connecting to a patient access site with a butterfly needle can include affixing the second region of a bandage to the front surface of the pair of wings of the butterfly needle. The butterfly needle can include a tip, a hub with a pair of wings extending radially therefrom, and tubing extending from the hub and in fluid communication with the tip. The bandage can be a pair of strips of flexible material. Each strip can have a first region, a second region, and a third region. The first region can have an adhesive on at least a surface portion thereof. The second region can also have an adhesive on at least a surface portion thereof. The second region can be affixed to the front surface of the one of the pair of wings of the butterfly needle. The third region can be arranged between the first and second regions and to contact a back surface of one of the pair of wings of the butterfly needle. The first region can be arranged so as to contact skin adjacent the patient access site when the second and third regions are coupled to the respective surfaces of the pair of wings of the butterfly needle inserted into the patient access site. The method can further include inserting the tip of the butterfly needle into the patient access site and affixing the first region of the each of the pair of strips onto skin of the patient adjacent the patient access site such that the third region of each strip contacts the respective back surface of the pair of wings.

In embodiments, a bandage can have a flexible material including a first region and a second region. The first region can have a first adhesive thereon and a viewing window portion without any adhesive. The viewing window portion can be configured such that a patient access site in which a needle is inserted is viewable through said window portion when the bandage is attached to the patient's skin. The second region can have a second adhesive thereon and a hole therein. The second region can be separated into a pair of longitudinally extending tabs by a cut extending from an end of the bandage to the hole. The hole can be constructed such that a part of the needle fits in said hole when the bandage is attached to the patient's skin.

In embodiments, a method for using a bandage can include positioning a viewing window of a bandage over a patient access site, which has a needle inserted therein. The method can further include adhering a first adhesive in a first region of the bandage to the patient's skin. Tabs in a second region of the bandage can be separated and tubing attached to the needle can be passed through a hole in the second region. The method can also include adhering a second adhesive of the tabs to the patient's skin.

Objects and advantages of embodiments of the present disclosure will become apparent from the following description when considered in conjunction with the accompanying drawings.

BRIEF DESCRIPTION OF DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 1 shows a butterfly needle to which a bandage may be applied to prevent removal of the needle from a patient access.

FIGS. 2A-2B show a front view and a side view, respectively, of a bandage for preventing removal of a needle from a patient access, according to one or more embodiments of the disclosed subject matter.

FIGS. 3A-3B show a front view and a side view, respectively, of the bandage of FIGS. 2A-2B in a first step of an application process to the butterfly needle of FIG. 1.

FIGS. 3C-3D show a front view and a side view, respectively, of the bandage of FIGS. 2A-2B in a second step of an application process to the butterfly needle of FIG. 1.

FIGS. 3E-3F show a front view and a side view, respectively, of the bandage of FIGS. 2A-2B in a third step of an application process to the butterfly needle of FIG. 1.

FIGS. 3G-3H show a front view and a side view, respectively, of the bandage of FIGS. 2A-2B in a fourth step of an application process to the butterfly needle of FIG. 1.

FIGS. 13A-13B show a front view and a side view, respectively, of the bandage of FIGS. 12A-12B applied to the butterfly needle of FIG. 1.

FIG. 14 shows a needle guard that can be used with a bandage, according to one or more embodiments of the disclosed subject matter.

FIGS. 27A-27B show a front view and side view, respectively, of a bandage for preventing removal of a needle from a patient access, according to one or more embodiments of the disclosed subject matter.

FIG. 28 shows a bandage applied to a butterfly needle together with a needle guard, according to one or more embodiments of the disclosed subject matter.

FIGS. 29A-29B show a front view and a side view, respectively, of the bandage of FIGS. 27A-27B applied to the butterfly needle of FIG. 1

FIG. 30 shows a side view of the butterfly needle inserted into a patient access with the bandage of FIGS. 27A-27B applied to the butterfly needle and securing the needle to the access.

DETAILED DESCRIPTION

Figure 3I:
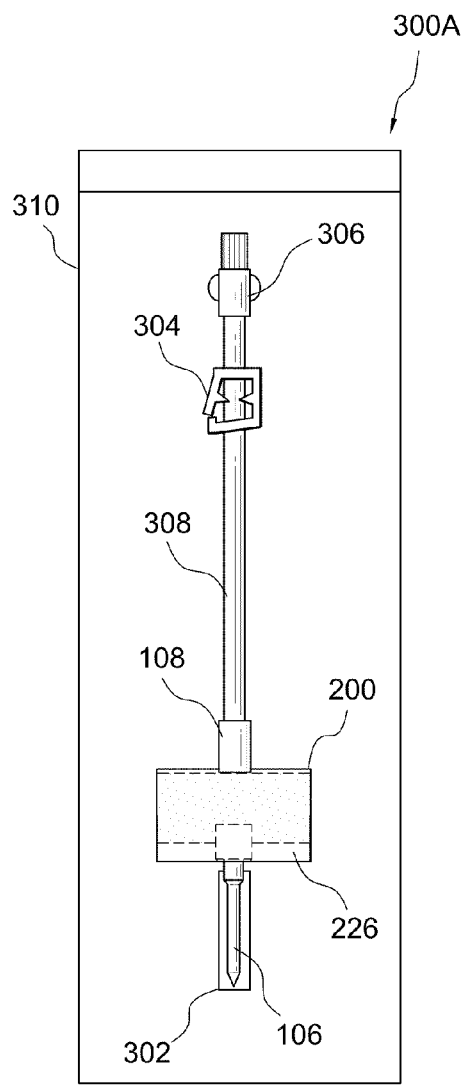
FIG. 3I shows a kit including a bandage assembled to a butterfly needle, according to one or more embodiments of the disclosed subject matter.

Butterfly needles can be used for transfusions, in particular for taking a blood sample, or for providing a treatment to a patient, such as a dialysis treatment. Such needles are termed butterfly needles on account of a pair of wings that extend radially from a hub of the needle. FIG. 1 shows an example of a butterfly needle 100. The needle 100 includes a tip 106 for piercing the skin of a patient and for providing fluid communication between an opening on the tip 106 and tubing 108. Tubing 108 can connect to other tubing, machines, or fluid receptacles, such as a blood sample vacuum tube. Tubing 108 is connected to the tip 106 by a hub 104. Hub 104 has a pair of wings 102 which extend radially from the hub.

By pressing the wings 102 together, handling of the needle 100 for insertion into an access site of the patient is facilitated. When the needle is inserted into a blood vessel or fistula, movement of the needle within the patient can lead to complications, such as phlebitis or hematoma. Moreover, inadvertent or unintentional removal of the needle from the patient access site can lead to blood loss from the patient or loss of medicament or fluids that were in the process of being administered to the patient. Accordingly, it is desirable to prevent movement of the butterfly needle once inserted into the patient access site.

A bandage 200 of flexible material can resist extraction and/or movement of the butterfly needle after insertion into the patient access site. Referring to FIGS. 2A-2B, bandage 200 can be made from a thin, flexible material, such as a polymer. For example, the bandage can be made from nylon fibers embedded in medical cloth. In another example, the bandage is made from a clear or transparent plastic material, such as a polyethylene film. Other materials may also be employed in accordance with one or more contemplated embodiments.

The bandage 200 can be separated into multiple regions by three fold lines. However, it should be appreciated that fewer or additional fold lines and/or regions can be used. A top end region 204 is demarcated by a first fold line 208. An adhesive 206 is provided on the top end region 204. The top end region 204 is arranged to be in contact with the skin of the patient when applied to a needle inserted into the patient. The top end region 204 also includes a portion 202 that is free from adhesive. The portion 202 can be used to remove the bandage 200 from the skin of the patient after use. Between the first fold line 208 and a second fold line 212 is an intermediate region 210. When the bandage 200 is applied to the needle 100, the intermediate region 210 is arranged so as to contact a front side of the wings 102 of the needle 100. However, since there is no adhesive applied to the intermediate region 210, the bandage does not adhere to the front side of the wings 102. Between the second fold line 212 and the third fold line 218 is a wing contact region 214. Wing contact region 214 has an adhesive 216 covering at least a portion of said region 214. The adhesive 216 is designed to releasably couple the bandage to wings 102 of the needle 100. When the bandage 200 is applied to the needle 100, the wing contact region 210 is arranged so as to contact a back side of the wings 102 of the needle 100. The adhesive 216 thereby couples the bandage 200 to the needle 100 for use on a patient. A bottom end portion is demarcated by the third fold line 218. The bottom end portion includes a pair of tabs 222 separated by a gap 220. Gap 220 may also extend into the wing contact region 214 so as to allow the tubing 108 to fit therethrough such that the wing contact region 214 can contact the entire back-side of the wings 102. The tabs 222 can be provided without any adhesive.

The top end region 204 can also include a clot promoting region, such as hemostasis pad 224. The hemostasis pad 224 can include, for example, a gel or gauze with clot promoting material thereon. Since the top end region 204 is arranged to be in contact with the skin of the patient, the hemostasis pad 224 can be positioned so as to contact the access site through which the needle 100 is inserted into the patient. When the needle 100 is removed from the patient access site, the hemostasis pad 224 contacts blood flowing from the access site to promote clotting (i.e., hemostasis).

Bandage 200 can be packaged separately from needle 100 and then assembled to the needle 100 prior to use. One or more covers can be provided on the areas of the bandage (for example, removably attached to the various adhesive regions of the bandage) to prevent inadvertent contact with a surface or the collection of dirt or other foreign objects thereon. Even when the bandage 200 is previously assembled to the needle 100, a cover may be provided to the regions of the bandage 200 intended for contact with a patient's skin. Covers for the bandage can be made from, for example, paper or a flexible polymer. For example, wing contact portion 214 can have a cover 228, which protects adhesive 216. Prior to assembly of the bandage 200 to the wings 102 of the needle 100, the cover 228 can be removed so as to expose adhesive 216. In addition, top end region 204 can have a cover 226, which protects adhesive 206 and hemostasis pad 224 in said region. Prior to application of the bandage 200 to the patient's skin, the cover 226 can be removed so as to expose the adhesive 206.

FIGS. 3A-3H show steps in an assembly of the bandage 200 to the needle 100. Referring to FIGS. 3A-3B, front and side views are shown of the wing contact region 214 contacting the back-side of wings 102. The adhesive 216 of the wing contact region 214 releasably attaches the bandage to the needle 100. In FIGS. 3C-3D, the bandage 200 is folded along third fold line 218 such that tabs 222 are arranged behind the wings 102. In FIGS. 3E-3F, the top end region 204 and the intermediate region 210 are folded down along second fold line 212. In FIGS. 3G-3H, the top end region 204 is then folded up along first fold line 208, resulting in a final assembled configuration.

Because of this configuration, cover 226 (not shown in FIGS. 3A-3H) can be maintained on the top end region 204 even when the bandage has been previously assembled to the needle 100. The cover 226 can be removed before or after insertion of the needle 100 into the patient access site. Moreover, the configuration can allow the top end region 204 to be applied to the skin after insertion of the needle by simply unfolding the bandage along first fold line 208 and placing the top region 204 into contact with the skin. The configuration can also allow positioning of the hemostasis pad 224 with respect to the patient access site.

Figure 3J:
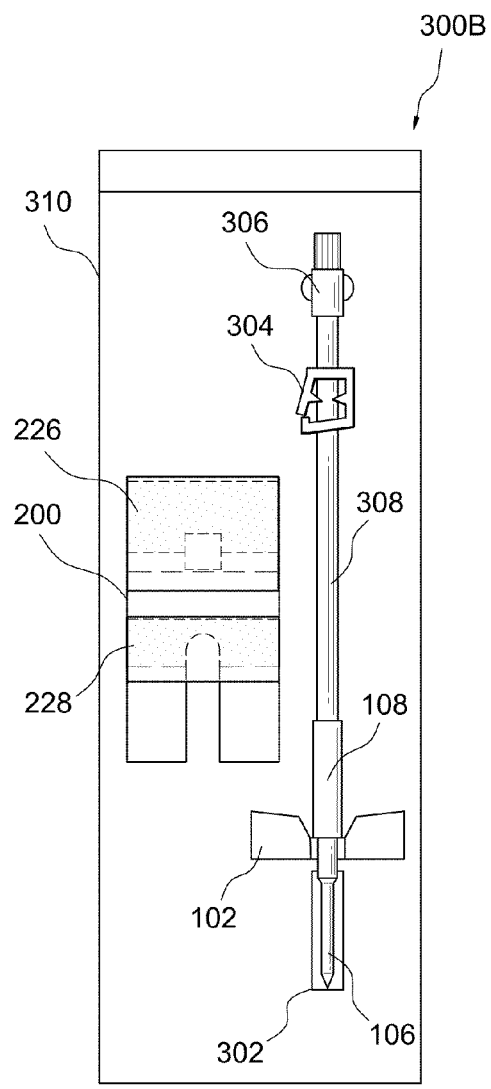
FIG. 3J shows an alternative kit including a bandage separate from a butterfly needle, according to one or more embodiments of the disclosed subject matter.

The needle 100 and the bandage 200 in the assembled configuration of FIGS. 3G-3H can be provided as part of a kit. Referring to FIG. 3I, a kit 300A for venipuncture can include a needle and bandage assembly that have been previously coupled together and sterilized in a bag 310 or other container. The tip 106 of the needle 100 can be protected by a cap 302 to prevent against inadvertent contact. Tubing 108 of the needle can be connected to an additional length of tubing 308. Alternatively, tubing 108 and tubing 308 can be combined into a single length of tubing. A clamp 304 can be provided on tubing 308 in order to stop the flow of fluids flowing through the tubing 308 and the needle 100. A connector 306 can also be provided for connecting the tubing 308 to a fluid receptacle, such as a blood sample container, or a treatment machine, such as a dialysis system. Cover 226 protects adhesive 206 of the top end region 204 of the bandage 200 prior to actual use. In an alternative configuration, a kit 300B for venipuncture can include the needle 100 and bandage 200 in an unassembled configuration, as shown in FIG. 3J. Prior to use, the cover 228 of the wing contact region 214 is removed to allow the bandage 200 to be applied to the needle 100, as shown in FIGS. 3A-3H.

Figure 4:
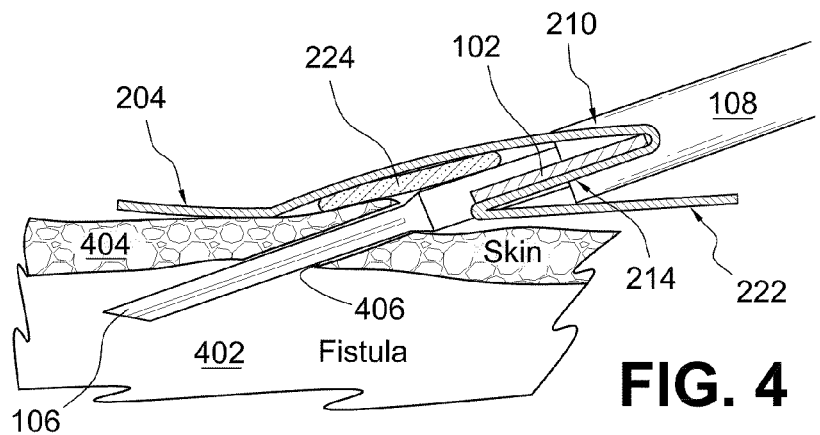
FIGS. 4-6 show various steps in the operation of the assembled bandage and butterfly needle of FIGS. 3G-3H during insertion and removal from a patient access, according to one or more embodiments of the disclosed subject matter.

When attached to the needle 100, the arrangement of the top end region 204 and the wing contact region 214 of the bandage 200 is such that the needle 100 is prevented from moving away from the patient access site. Referring to FIG. 4, a needle-bandage assembly used in accessing a fistula 402 is shown. The wing contact region 214 of the bandage 200 is attached to the back-side of the wings 102 prior to inserting the needle 100 into the patient. The tip 106 of the needle 100 can be inserted into the patient by piercing the skin 404 through an access site 406. The bandage 200 loops over the front-side of the wings 102 such that the intermediate region 210 may be in contact with at least a portion of the front-side of the wings 102. The top end region 204 can be attached to the skin 404 of the patient and can hold the needle-bandage assembly in place with the needle 100 inserted into the patient access site 406.

Figure 5:
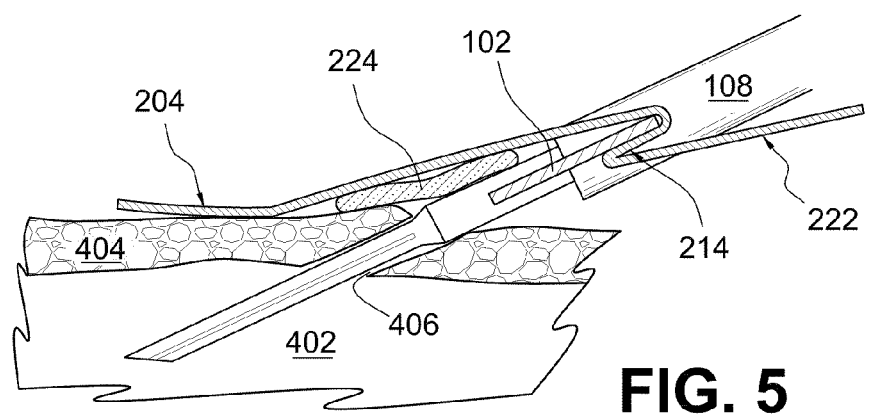
Figure 6:
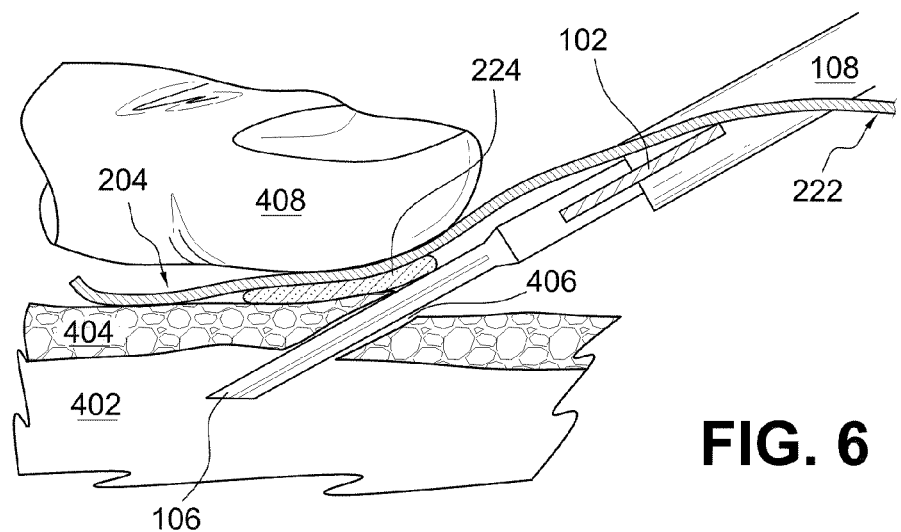

When it is desired to remove the needle 100 from the patient, the bandage can be released from the needle 100. Referring to FIG. 5, the wing contact region 214 can be released from the wings 102 by pulling on tabs 222. This action peels the bandage from the wings 102 while the needle 100 remains in place. Once the wing contact region 214 of the bandage 200 is removed from the butterfly needle 100, the needle 100 can be freely withdrawn from the access site while the bandage 200 remains in contact with the patient's skin, as shown in FIG. 6.

As blood is likely to exit through the patient access site 406 when it is vacated by the needle, a user may apply finger pressure 408 to contact the hemostasis pad 224 with the patient access site 406 as the needle 100 is removed to promote clotting at the access site. Once the needle 100 is fully removed, finger pressure 408 may be maintained to contact the hemostasis pad 224 with the access site 406 until bleeding has stopped. Alternatively, once the needle 100 is fully removed, alternative means of applying continued pressure against the hemostasis pad 224 and the access site 406 may be used. For example, an additional bandage or tape may be applied to maintain pressure against the hemostasis pad 224 to promote hemostasis. The bandage 200 can be further secured to the skin 404 by the wing contact region 214 in addition to the top end region 204 so as to keep the hemostasis pad 224 in place over the patient access site 406. In another example, an air-filled bubble can be taped over the bandage 200 such that the bubble continues to apply pressure to the access site 406 through the bandage 200.

Figure 7A:
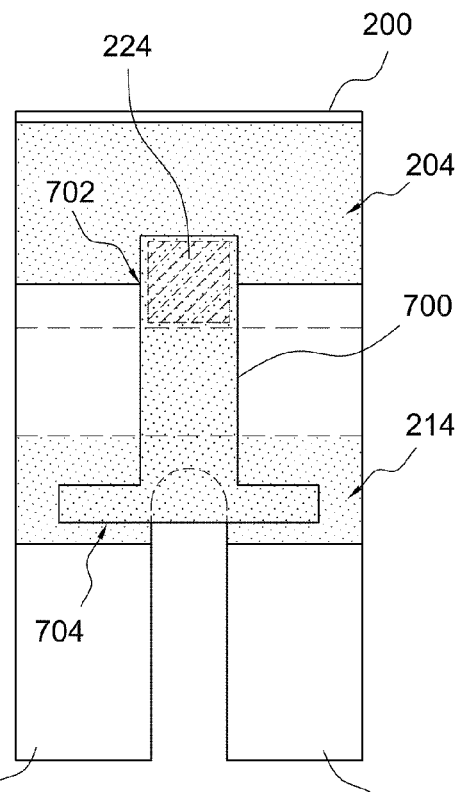
FIGS. 7A-7B show a front view and a side view, respectively, of a bandage with hemostasis pad cover, according to one or more embodiments of the disclosed subject matter.
Figure 7B:
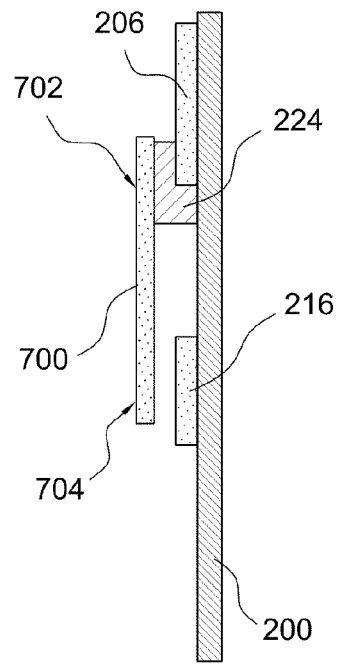
Figure 8A:
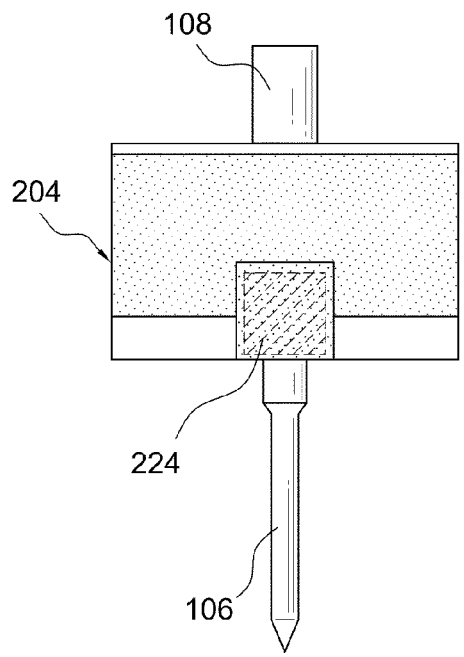
FIGS. 8A-8B show a front view and a side view, respectively, of the bandage of FIGS. 7A-7B applied to the butterfly needle of FIG. 1.
Figure 8B:
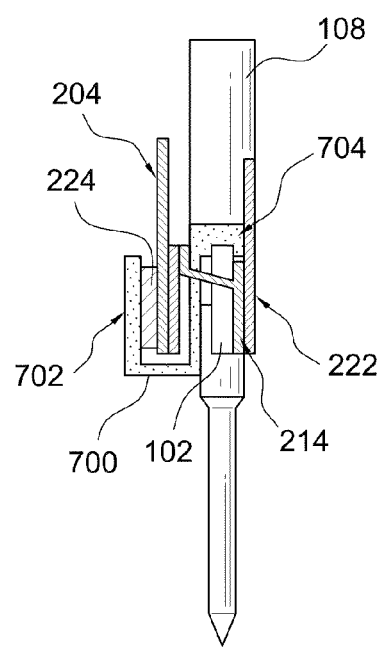

Since the hemostasis pad 224 is not in use until the needle 100 is actually removed from the patient access site 406, a separate cover can be provided for the hemostasis pad. Referring to FIGS. 7A-7B, a bandage 200 with a hemostasis pad cover 700 is shown. The hemostasis pad cover 700 can include a covering portion 702 which protects the hemostasis pad 224 prior to removal of needle 100 from the patient access site. The hemostasis pad cover 700 can also include a portion that attaches to the needle. For example, the hemostasis pad cover 700 can include a winged portion 704 that can wrap around the tubing 108 or a portion of the hub 104 of the needle 100. Alternatively or additionally, portion 704 can include adhesive to couple the hemostasis pad cover 700 to the needle. The bandage 200 with a hemostasis pad cover 700 assembled to a needle 100 is shown in FIGS. 8A-8B.

Figure 9:
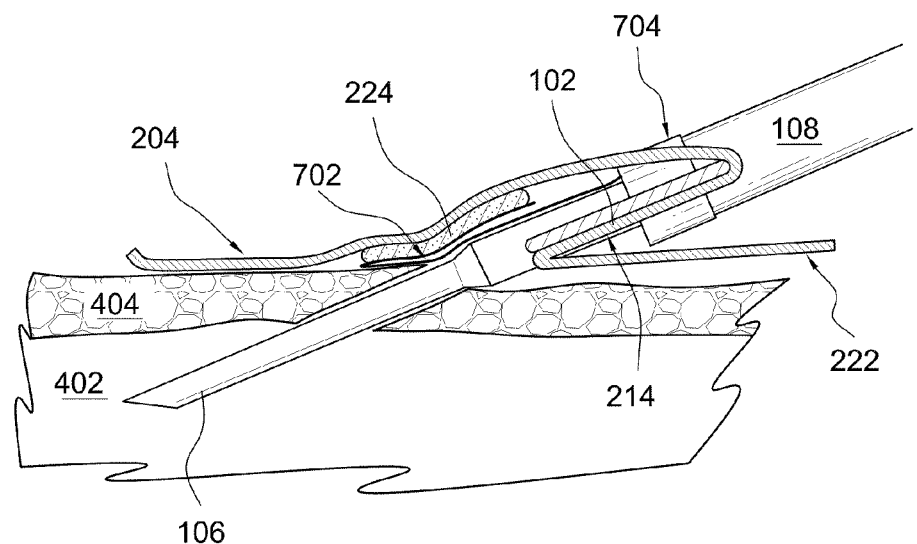
FIGS. 9-10 show various steps in the operation of the assembled bandage and butterfly needle of FIGS. 8A-8B during insertion and removal from a patient access, according to one or more embodiments of the disclosed subject matter.
Figure 10:
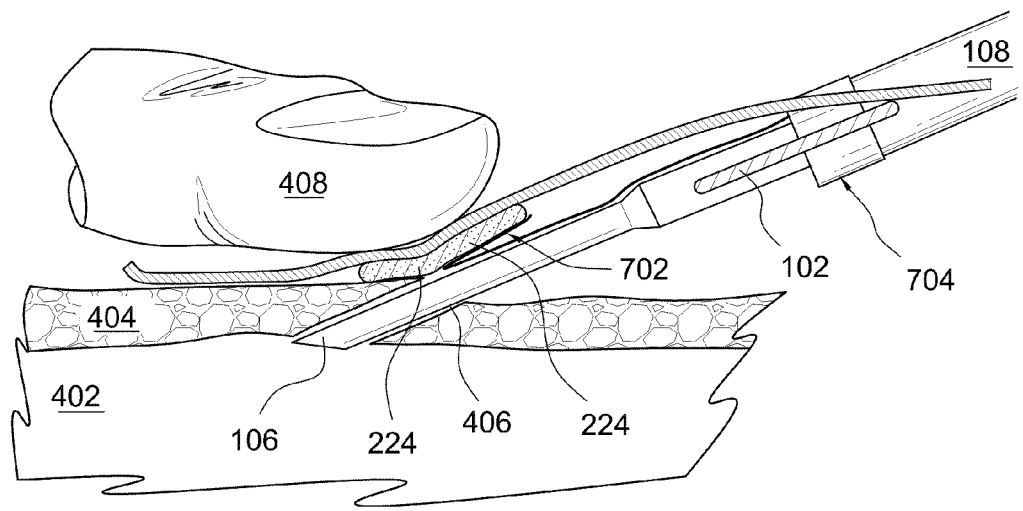

FIG. 9 shows the bandage 200 with hemostasis pad cover 700 assembled to a needle 100, which is inserted into a patient access site 406. Covering portion 702 of the hemostasis pad cover 702 can remain in place to protect the hemostasis pad 224 until needle extraction from the access site 406. Winged portion 704 can be wrapped around the circumference of the tubing, thereby coupling the hemostasis pad cover 700 to the needle 100. Referring to FIG. 10, as the needle 100 is removed from the patient access site 406 while keeping bandage 200 in place, the covering portion 702 can be simultaneously removed from the hemostasis pad 224, thereby exposing the hemostasis pad 224 to the patient access site 406.

Figure 11:
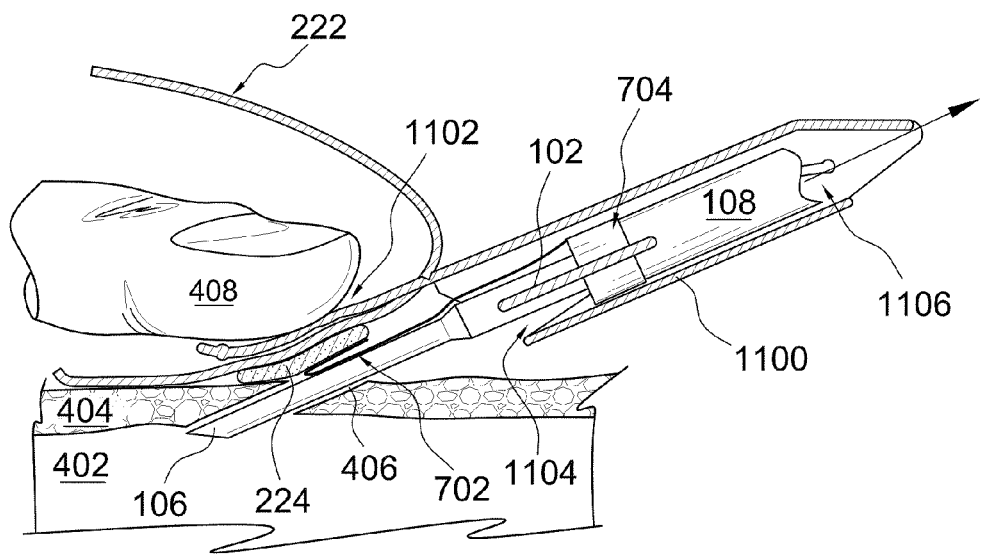
FIG. 11 shows a removal step of an assembled bandage and butterfly needle with needle guard, according to one or more embodiments of the disclosed subject matter.

Because of the danger of disease transmission and/or risk of injury to those handling used needles (such as medical staff or medical waste handlers), safety devices can be employed to avoid accidental touching or pricking of the handlers by the used needle. For example, a needle guard 1100 may be used to contain the needle after use. Referring to FIG. 11, bandage 200 is shown in use with such a needle guard 1100. Needle guard 1100 can be movably coupled to the tubing, which extends through an opening at a rear portion of guard 1100. During insertion and use of the needle, the needle guard 1100 can be maintained at a position along the tubing 108 remote from the patient access site 406. When it is desired to remove the needle 100, the wing contact region 214 of bandage 200 can be released from the wings 102 of the needle 100, and the needle guard 1100 can be moved into place proximal to the patient access site 406.

The needle guard can include a front opening 1104 through which the needle 100 and tubing 108 can pass. A locking region 1106 can be provided at the rear of the needle guard 1100. As the needle 100 is removed from the access site 406, it progresses into the opening 1104 and into the body of the needle guard 1100. At the rear of the needle guard 1100, the wings 102 of the needle can be captured by the locking region 1106, thereby preventing further motion of the needle 100 into or out of the needle guard 1100. The needle guard 1100 can be sized and shaped such that the tip 106 of the needle is fully contained within the body of the needle guard 1100 when the wings 102 of the needle 100 are captured by the locking region 1106, thereby preventing inadvertent contact with needle tip 106. Needle guard 1100 may further include a finger guard 1102. The finger guard 1102 can be sized and shaped so as to allow finger pressure 408 to be applied to the hemostasis pad 224 and the access site 406 underneath when the needle guard 1100 is in position. The finger guard 1102 may be detachable such that finger pressure 408 may continue to be applied even when the needle guard 1100 with needle 100 therein is removed for disposal.

Figures 12A, 12B:
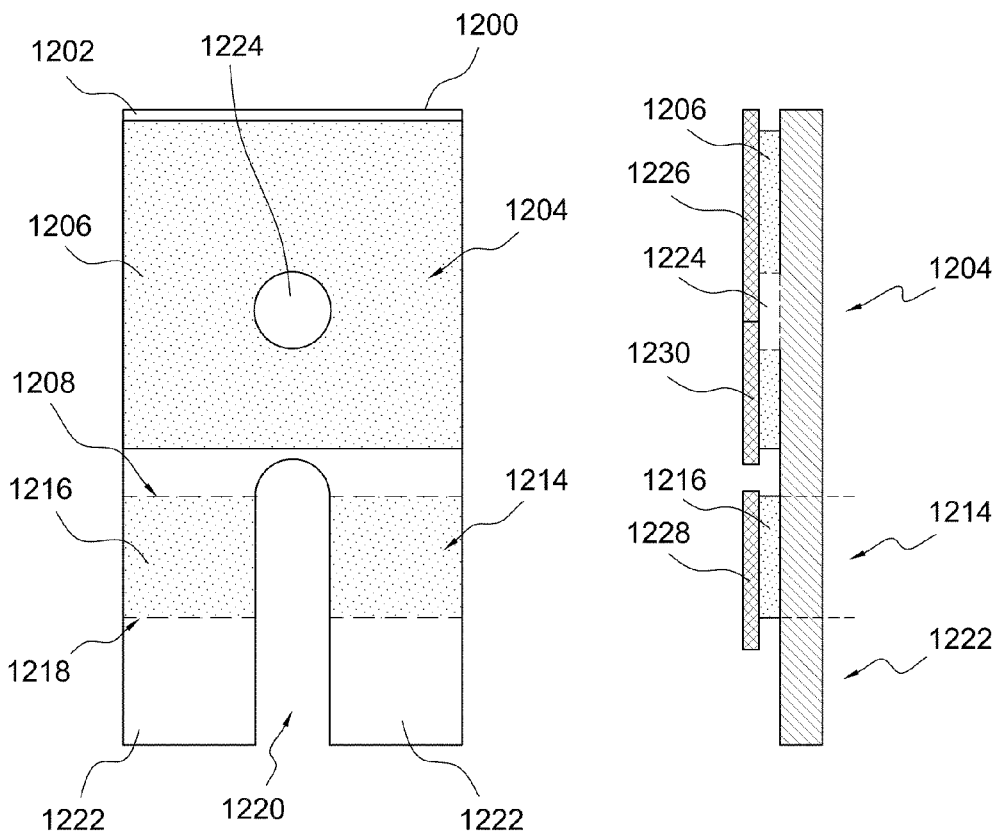
FIGS. 12A-12B show a front view and a side view, respectively, of a bandage with access site viewing window, according to one or more embodiments of the disclosed subject matter.

A bandage for securing the butterfly needle can include a viewing window that is arranged over the patient access site in order to provide a view thereof. For example, bandage 1200, as shown in FIGS. 12A-12B, has a viewing window 1224. Bandage 1200 can be made from a thin, flexible material, such as a polymer. For example, the bandage can be made from a clear or substantially transparent plastic material, such as a polyethylene film. Other materials may also be employed in accordance with one or more contemplated embodiments.

The bandage 1200 can be separated into multiple regions by one or more fold lines. However, it should be appreciated that fewer or additional fold lines and regions can be used. As shown in FIGS. 12A-12B, a top end region 1204 can be demarcated by a first fold line 1208. An adhesive 1206 can be provided on the top end region 1204. The top end region 1204 can be arranged for contact with the skin of the patient when applied to a needle inserted into the patient. The top end region 1204 can also include an optional portion 1202 that is free from adhesive. The portion 1202 can then be used to remove the bandage 1200 from the skin of the patient after use. The top end region 1204 can also include a viewing window region, such as window 1224. This window 1224 may be an adhesive-free region and can be substantially transparent to allow a relatively unobstructed view of the scene on the opposite side of the window 1224. Since the top end region 1204 is arranged to be in contact with the skin of the patient, the window 1224 is positioned over the access site through which the needle 100 is inserted into the patient. The window 1224 thus allows medical personnel or a patient to view the access site, for example, to monitor for complications.

Between the first fold line 1208 and a second fold line 1218 is a wing contact region 1214. Wing contact region 1214 can have an adhesive 1216 covering at least a portion thereof. The adhesive 1216 can be designed to releasably attach the bandage to wings 102 of the needle 100. When the bandage 1200 is applied to the needle 100, the wing contact region 1210 is arranged so as to contact a back side of the wings 102 of the needle 100. The adhesive 1216 thereby couples the bandage 1200 to the needle 100 for use on a patient. A bottom end portion can be demarcated by the second fold line 1218. The bottom end portion can include a pair of tabs 1222 separated by a gap 1220. Gap 1220 may also extend into the top end region 1204 and wing contact region 1214. The tabs 1222 can be provided without any adhesive.

As discussed herein, one or more covers can be provided on the bandage to prevent inadvertent contact with a surface or the collection of dirt or other foreign objects. Even when the bandage 1200 is assembled to the needle 100 prior to use, one or more covers can be provided to that region of the bandage 1200 meant for contact with a patient's skin. Such covers can be made from, for example, paper or a flexible polymer. For example, wing contact portion 1214 may have a cover 1228, which protects the adhesive 1216. Prior to assembly of the bandage 1200 to the wings 102 of the needle 100, the cover 1228 can be removed, thereby exposing the adhesive 1216. In addition, top end region 1204 can have a cover 1226, which protects a top part of the adhesive 1206 in said region. Prior to application of the bandage 1200 to the patient's skin, the cover 1226 can be removed, thereby exposing the top portion of adhesive 1206. The bottom portion of the adhesive 1206 can have a separate cover 1230. The bottom portion of the adhesive 1206 can be exposed after removal of the needle 102 to adhere the remainder of the top end region 1204 to the skin, thereby surrounding the patient access site. The bandage 1200 assembled to a needle 100 is shown in FIGS. 13A-13B.

Figure 15:
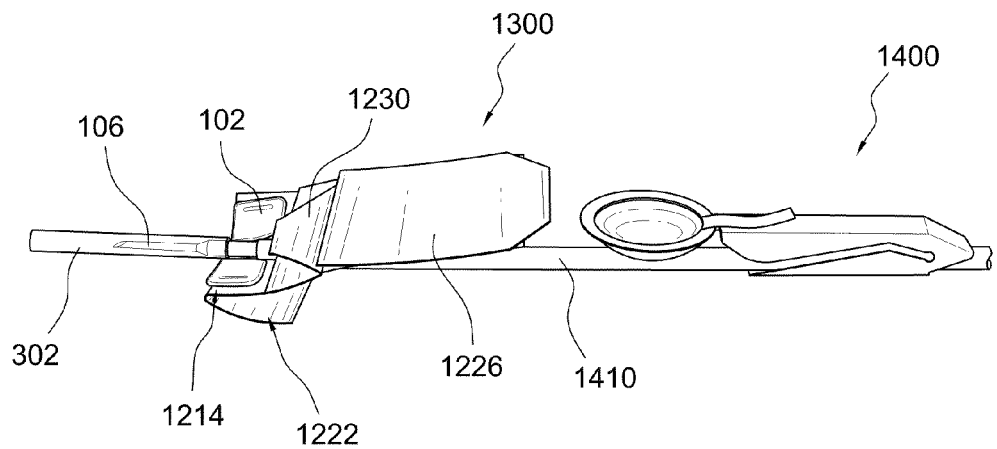
FIGS. 15-16 shows of a perspective view and a top view, respectively, of the assembled bandage and butterfly needle of FIG. 13A-13B together with the needle guard of FIG. 14.
Figure 16:
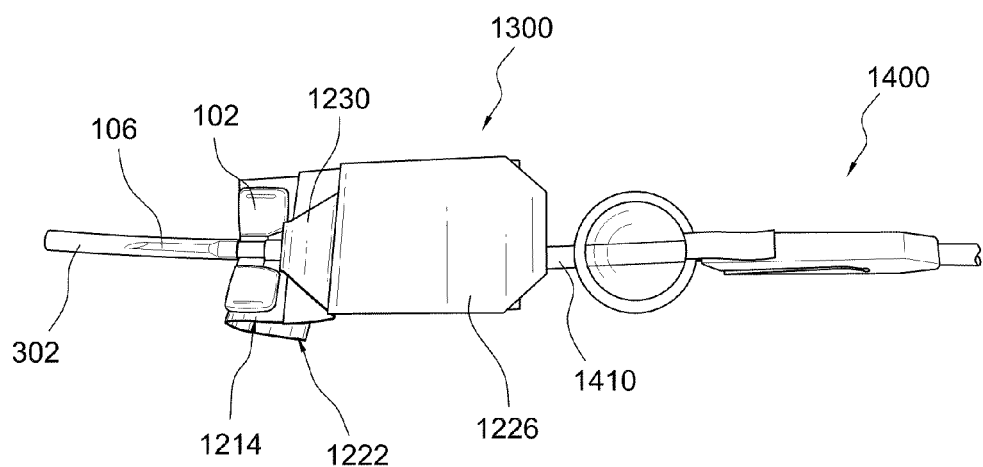

Referring to FIGS. 14-16, an assembly with a needle guard 1400 and a bandage 1200 for a butterfly needle 100 is shown. Needle guard 1400 can be movably coupled to the tubing 1410, which extends through an opening at a rear 1408 thereof. During insertion and use of the needle, the needle guard 1400 can be maintained at a position along the tubing 1410 remote from the patient access site. When it is desired to remove the needle 100, the wing contact region 1214 of bandage 1200 can be released from the wings 102 of the needle 100, and the needle guard 1400 can be moved into place proximal to the patient access site.

The needle guard can include a front opening 1404 through which the needle 100 and tubing 1410 can pass. A locking region 1406 can be provided at the rear of the needle guard 1400. As the needle 100 is removed from the access site, it can progress into the opening 1404 and into the body of the needle guard 1400. At the rear of the needle guard 1400, the wings 102 of the needle can be captured by the locking region 1406, thereby preventing further motion of the needle 100 into or out of the needle guard 1400. The needle guard 1400 can be appropriately sized and shaped such that the tip 106 of the needle is fully contained within the body of the needle guard 1400 when the wings 102 of the needle 100 are captured by the locking region 1406, thereby preventing inadvertent contact with said tip 106.

Needle guard 1400 may further include a bowl-shaped finger guard 1402. The finger guard 1402 can be sized and shaped so as to allow finger pressure to be applied to the access site when the needle guard 1400 is in position. The finger guard 1402 can be detachable such that finger pressure can be continuously applied even when the needle guard 1400 with needle 100 therein is removed for disposal. For example, finger guard 1402 can be attached to the top surface 1414 of the needle guard 1400 by a piece of tape 1412. Alternatively, finger guard 1402 can be attached to the needle guard 1400 by a frangible or break-away portion of the needle guard 1400.

Figure 17:
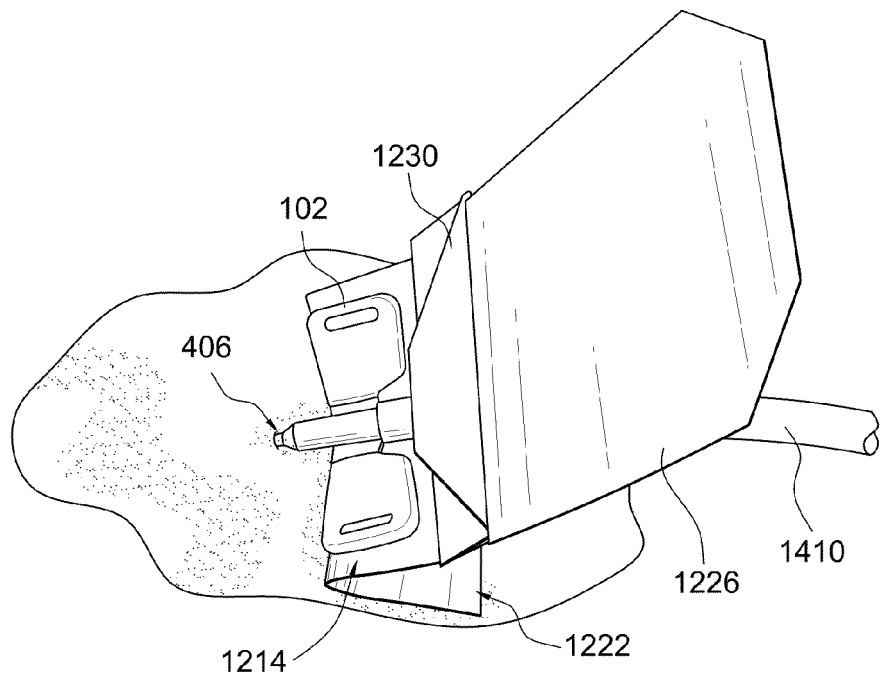
FIGS. 17-24 show various steps in the operation of the assembled bandage, butterfly needle, and needle guard of FIGS. 15-16 during insertion and removal from a patient access, according to one or more embodiments of the disclosed subject matter.
Figure 18:
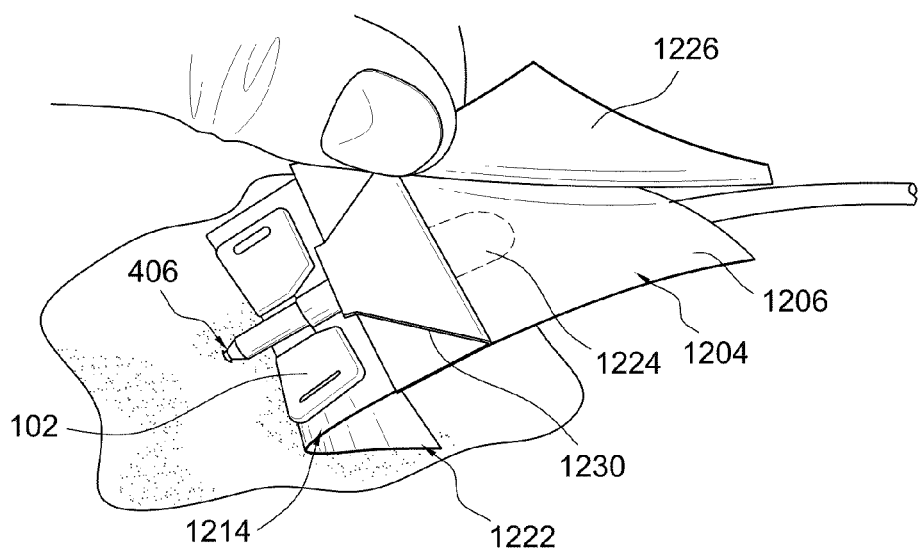
Figure 19:
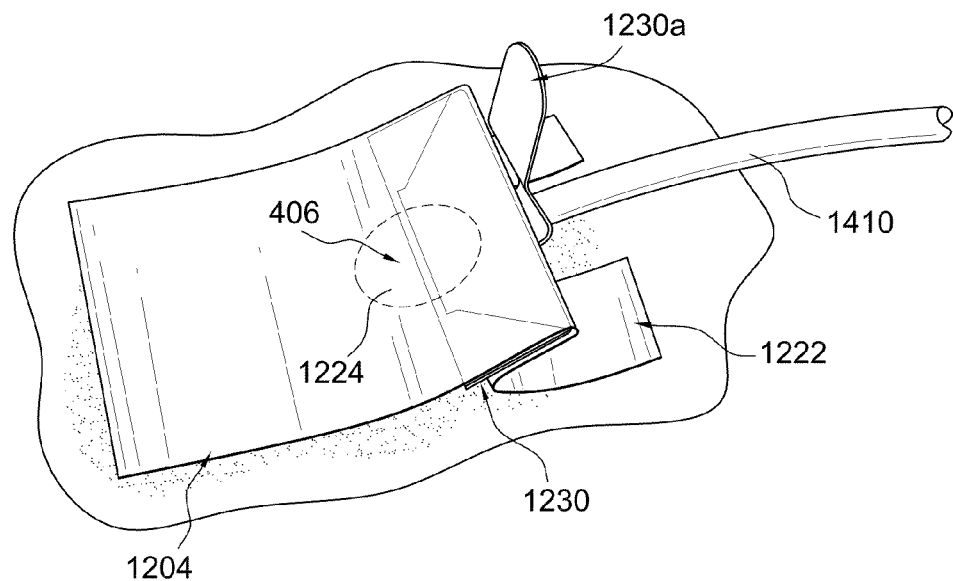

When attached to the needle 100 and the patient, the arrangement of the top end region 1204 and the wing contact region 1214 of the bandage 1200 prevents the needle 100 from moving away from the patient access site 406. The wing contact region 1214 of the bandage 1200 can be attached to the back-side of the wings 102. The needle 100 can then be inserted into the patient access site 406, as shown in FIG. 17. Cover 1226 can be removed thereby exposing the top portion of adhesive 1206 in top end region 1204, as shown in FIG. 18. Cover 1230 can remain in place until the needle 100 is removed from the patient access site 406. The top end region 1204 can be looped over the front-side of the wings 102 by folding along fold line 1208. Cover 1230 can thus be in contact with at least a portion of the front-side of the wings 102. The top end region 1204 can be attached to the skin of the patient so as to hold the needle-bandage assembly in place while the needle 100 inserted into the patient access site 406, as shown in FIG. 19. Window 1224 can be positioned over patient access site 406 to allow medical personnel or the patient to view the needle in the access site.

Figure 20:
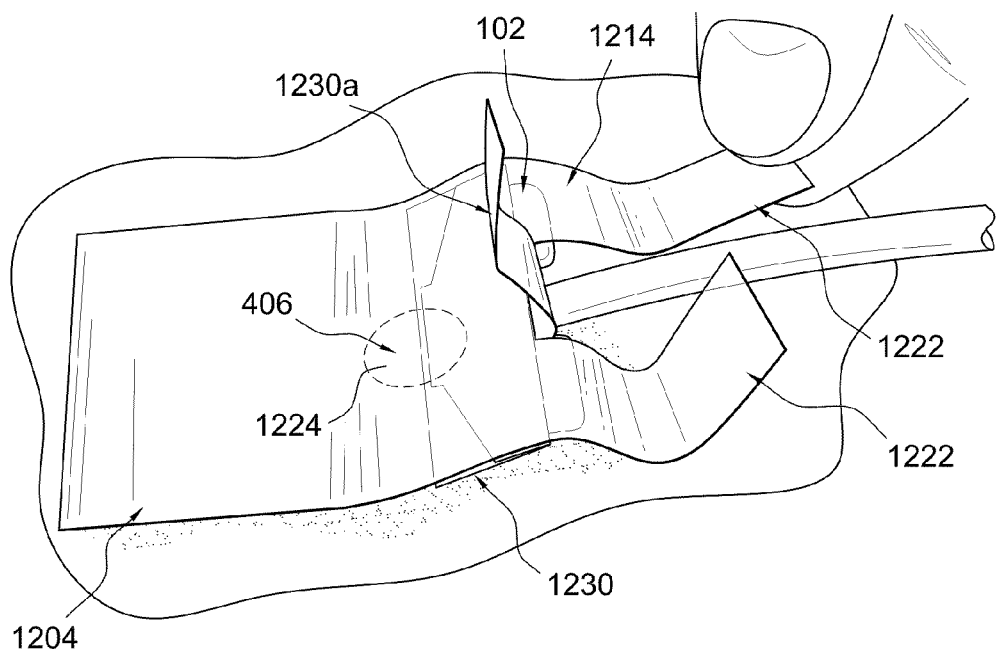
Figure 21:
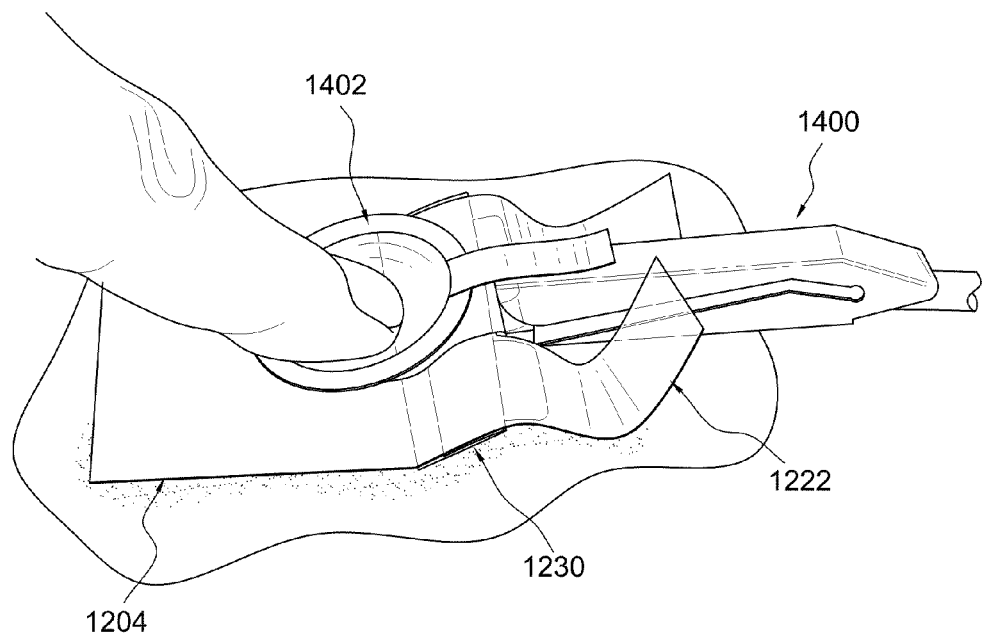
Figure 22:
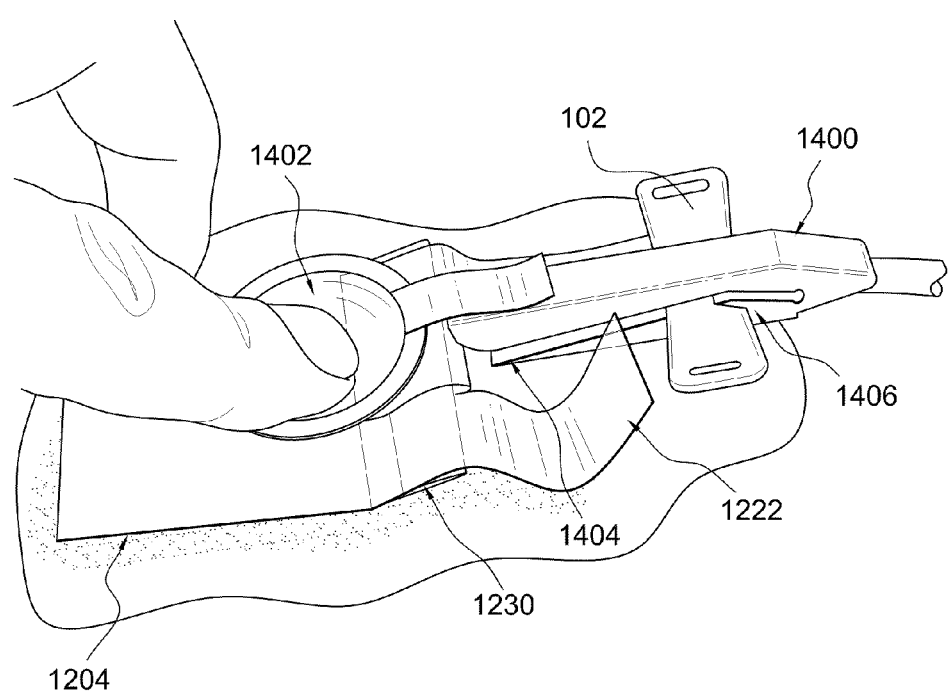
Figure 23:
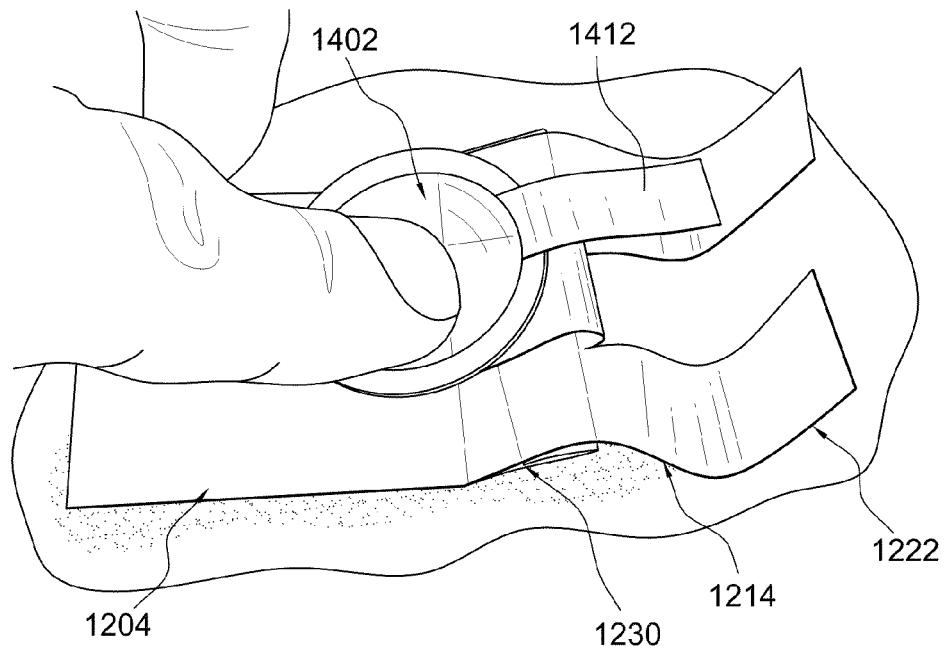
Figure 24:
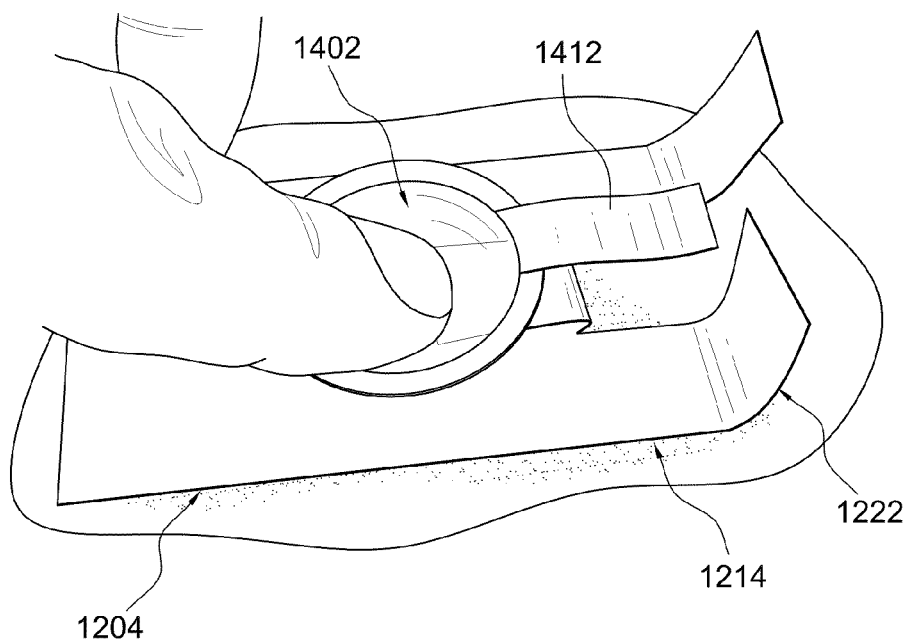

When it is desired to remove the needle 100 from the patient, the bandage 1200 can be released from the needle 100. The wing contact region 1214 may be released from the wings 102 by pulling on tabs 1222, as shown in FIG. 20. This action peels the bandage from the wings 102 while the needle 100 remains in place in the patient access. Once disconnected from the bandage, in particular, region 1204, the needle 100 can be removed while the bandage 1200 remains in contact with the patient's skin. The needle guard 1400 can be moved into position proximal to the patient access site 406 prior to removing the needle 100, as shown in FIG. 21. Finger pressure can be applied to the patient access site 406 by pushing on finger guard 1402. Needle 100 can then be removed by pulling on tubing 1410 until the needle is retracted into the needle guard, as shown in FIG. 22. The finger guard 1402 can be detached from the needle guard 1400 by removing tape 1412. The needle guard 1400 with needle 100 therein can be moved from the patient access site while pressure is maintained on the patient access site 406, as shown in FIG. 23. The bandage 1200 can be fully applied to the skin by removing cover 1230 from the remainder of the top end region 1204. A tab 1230a (see FIG. 19) can be provided to easily remove the cover 1230 from the bandage 1200, after which all of the top end region 1204 can be affixed to the skin of the patient so as to surround the patient access site 406, as shown in FIG. 24.

Figure 25:
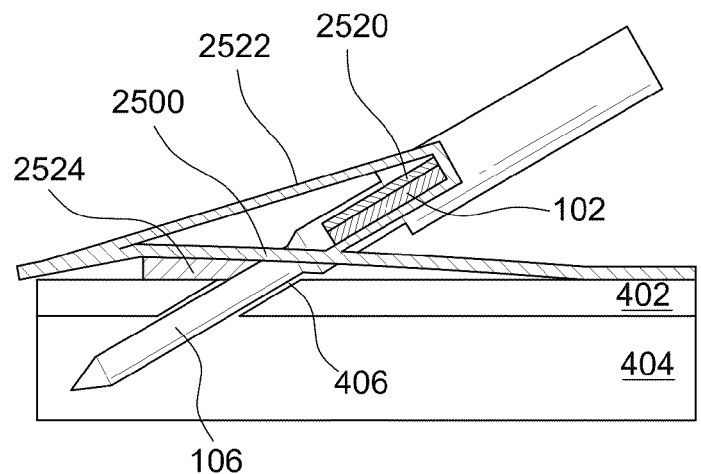
FIGS. 25-26 shows a side view and a top view, respectively, of an alternative bandage with hemostasis pad in use, according to one or more embodiments of the disclosed subject matter.
Figure 26:
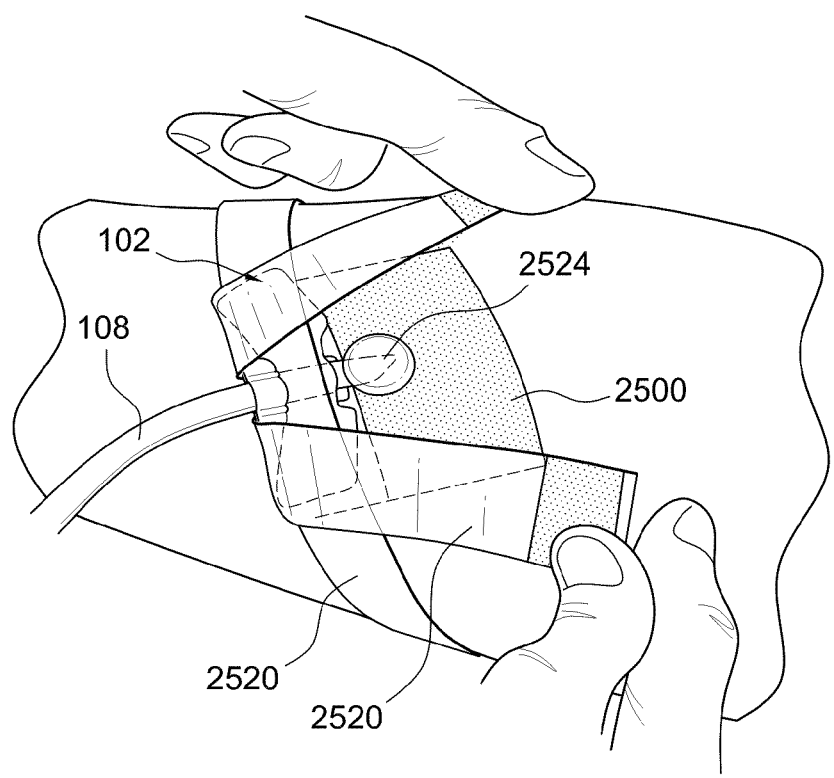

Concepts and features of the disclosed embodiments can be applied to other configurations of bandages for securing needles and/or promoting hemostasis. For example, the disclosed hemostasis pad may be combined with other types of securing bandages to promote hemostasis after removal of the needle. Referring to FIGS. 25-26, an embodiment of a bandage for securing a needle 100 to a patient access site is shown. The bandage has a skin-contact portion 2500 with a hemostasis pad 2524 arranged so as to contact the patient access site 406, through which the tip 106 of needle 102 is inserted. The skin-contact portion 2500 is positioned under the wings 102 of the needle. To hold the wings 102 of the needle 100 against the skin, a separate piece of tape or bandage 2520 is provided. The tape 2520 extends over the top surface of the wings 102 of the needle and exerts a force on the wings 102 holding the wings against the skin of the patient. The bandage also includes two tab regions 2522 with adhesive on an end thereof. The tab regions 2522 loop around the back-side of the wings and are adhered to the skin proximal to skin-contact region 2500. This configuration of the tab regions 2522 looped around the wings 102 thus prevents inadvertent withdrawal of the needle from the patient access site 406. When it is desired to remove the needle 100, the tab regions 2522 can be peeled from the skin, and the tape 2520 can subsequently be removed. The needle 100 can thus be removed from the patient access site while the skin-contact portion 2500 remains in place. The hemostasis pad 2524 is in contact with the patient access site 406 as the needle is removed therefrom.

In another embodiment, the needle can be secured using a bandage that is attached to the needle wings and looping the bandage over the wings to attach to the skin. For example, two strips of medical tap can be used to secure the needle using a looping arrangement with respect to the needle wings. Such strips 2200A, 2200B are shown in FIGS. 27A-27B. Each strip 2200A, 2200B can be made from a thin, flexible material, such as a polymer. Each bandage strip 2200A, 2200B can be separated into multiple regions by two fold lines. However, it should be appreciated that fewer or additional fold lines and/or regions can be used. A top end region 2204 is demarcated by a first fold line 2208. An adhesive 2206 is provide in at least the top end region 2204, but can also extend to the other regions of the strip 2200 as shown. Alternatively, one or more of the regions 2204, 2210, and 2214 may be provided with a different adhesive or no adhesive at all in accordance with the teachings of the present disclosure. In addition, certain adhesives may be employed where contact with patient's skin is likely so as to avoid potential patient allergic reactions while other regions may employ different adhesives. The top end region 2204 can be arranged to be in contact with the skin of the patient when applied to a needle inserted into the patient. The top end region 2204 can also include a portion 2202 that is free from adhesive. The portion 2202 can then be used to remove the strip 2200 from the skin of the patient after use.

Between the first fold line 2208 and a second fold line 2212 is an intermediate region 2210. When the bandage 2200 is applied to the needle 100, the intermediate region 2210 is arranged so as to contact a back-side of the wings 102 of the needles, as shown in FIG. 29B. Adhesive may be applied to the intermediate region 2210. Optionally, adhesive in region 2210 may be omitted. Between the second fold line 2212 and the other end of strip 2200 is a wing contact region 2214. Wing contact region 2214 can have an adhesive covering at least a portion of said region 2214. The adhesive in region 2214 can be the same adhesive 2206 as in region 2204. Alternatively, the adhesive in region 2214 can be different from the adhesive in region 2204. The adhesive in region 2214 can be designed to attach the bandage to wings 104 of the needle 100. When the strip 2200 is applied to the needle 100, the wing contact region 2214 is arranged so as to contact a front-side of the wings 102 of the needle 100, as shown in FIGS. 29A-29B. The adhesive 2206 in region 2214 thereby couples the strip 2200 to the needle 100 for use.

Strips 2200 can be packaged separately from needle 100 and then assembled to the needle 100 prior to use. One or more covers can be provided for the strips to prevent inadvertent contact with a surface or the collection of dirt or other foreign objects. When the strips 2200 are assembled to the needle 100 prior to use, a cover can remain on the region of the strips 2200 meant for contact with the patient's skin. Such covers may be made from, for example, paper or a flexible polymer. For example, wing contact region 2214 and intermediate region 2210 can have a cover 2228 which protects the adhesive 2206 in those regions. Prior to assembly of the strips 2200 to the wings of the needle 100, the cover 2228 can be removed, thereby exposing the adhesive in regions 2214 and 2210. Region 2214 can then be adhered to the front-side of one of the wings while region 2210 of strip 2200 can be adhered to the back-side of one of the wings, with region 2204 extending away from the tip 106 of needle 100, as shown in FIGS. 28-29B. Top end region 2204 can have an additional cover 2224, which protects the adhesive 2206 in said region. Prior to application of the strip 2200 to the patient's skin, the cover 2224 can be removed, thereby exposing the adhesive 2206 in the top end region 2204.

Figure 31:
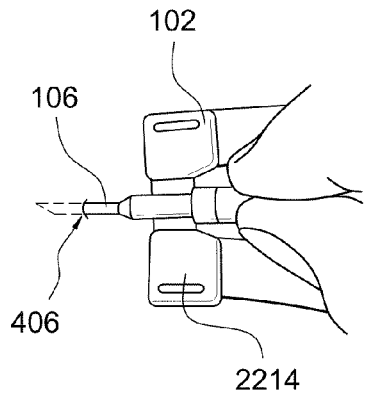
FIGS. 31-34 show various steps in the securing of the bandage of FIGS. 27A-27B to the patient skin after insertion of the butterfly needle.
Figure 32:
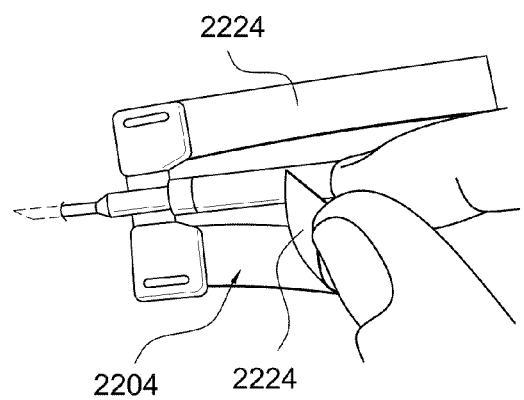
Figure 33:
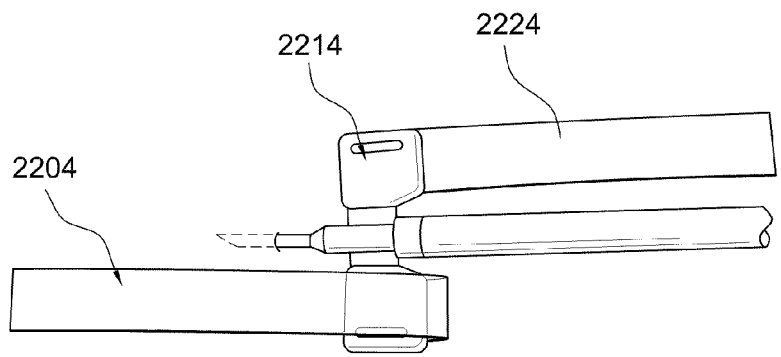
Figure 34:
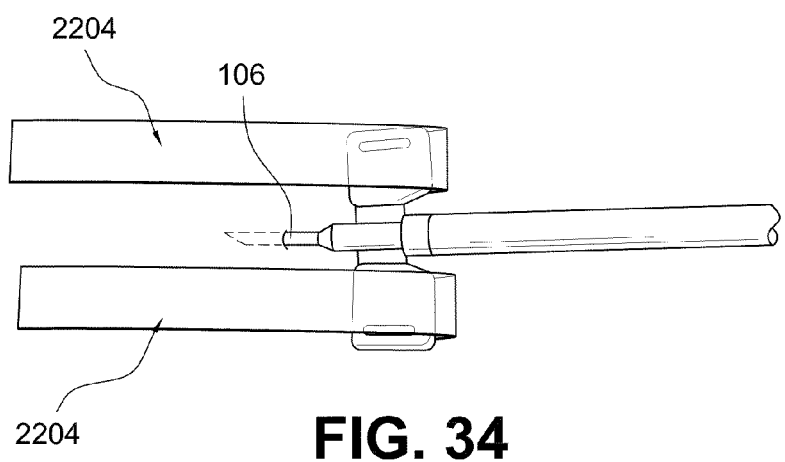

When attached to the needle 100, the arrangement of the top end region 2204 and the wing contact region 2214 of each strip 2200 can prevent needle 100 from moving away from the patient access site. Referring to FIG. 30, a needle-bandage assembly using the bandage strips of FIGS. 27A-27B is shown. At least the wing contact region 2214 of each strip 2200 can be attached to the front-side of the wings 102 prior to insertion of the needle 100 into the patient. The intermediate region 2210 can also be attached to the back-side of the wings 102 prior to insertion of the needle 100. The tip 106 of the needle 100 can be inserted into the patient by piercing the skin 402 to connect to an access site 406, as shown in FIG. 31. As shown in FIG. 32, the cover 2224 can be removed from the top end region 2204 before attaching the top end region to the patient skin. Referring to FIGS. 32-33, each strip 2200 loops behind the wings and then over the front-side of the wings 102 with the intermediate region 2210 in contact with at least a portion of the back-side of the wings 102. The top end region 2204 of each strip 2200 is attached to the skin 402 of the patient and holds the needle-bandage assembly in place with the needle 100 inserted into the patient access site 406, as shown in FIG. 34.

Figure 35:
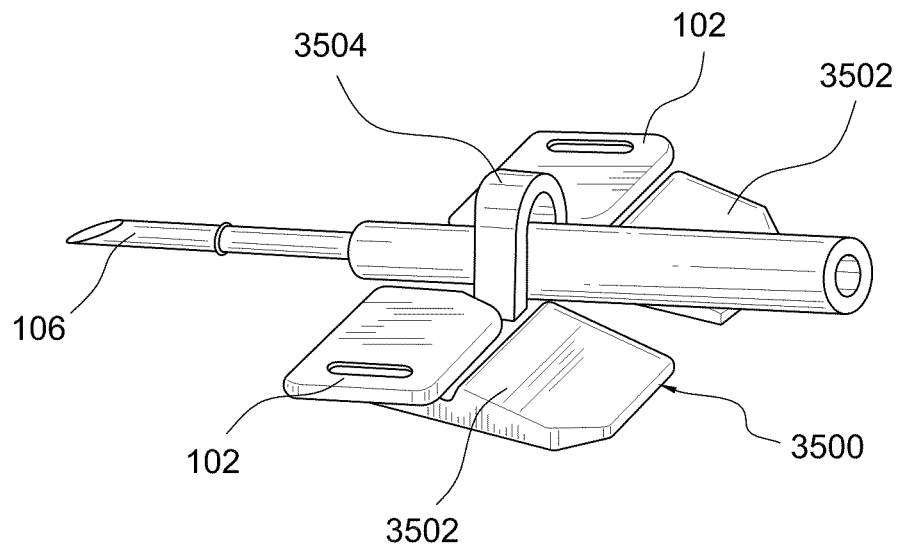
FIG. 35 shows a needle securing device together with a butterfly needle, according to one or more embodiments of the disclosed subject matter.

FIG. 35 shows a needle securing device 3500 with needle 100. Securing device 2500 can include separate wedge-shaped portions 3502 held together by a strap 3504, through which the tube 108 of needle 100 passes. A bottom surface of the wedge-shaped portion can be designed to sit on top of the patient's skin. A first top surface region of the wedge-shaped portion can be inclined or angled with respect to the bottom surface so as to contact the wings 102 of the needle, thereby abutting the ends of the wings 102 and preventing withdrawal of the needle from the patient access site. To secure the securing device in place against the patient skin, tape can be applied against to a second top surface region of the wedge-shaped portion.

Figure 36:
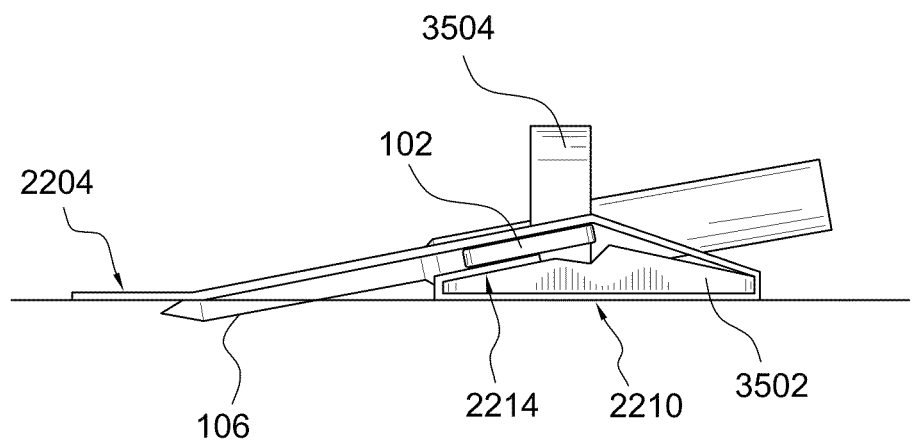
FIG. 36 shows a side view of the butterfly needle inserted into a patient access with the bandage of FIGS. 27A-27B applied to the needle securing device of FIG. 35.
Figure 37:
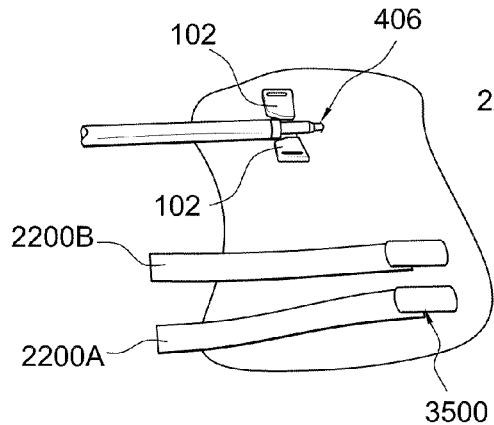
FIGS. 37-40 show various steps in the securing of the bandage of FIGS. 27A-27B with the needle securing device to the patient skin after insertion of the butterfly needle.

The bandage configuration of FIGS. 27A-27B can also be applied to the securing device-needle assembly to secure the assembly to a patient access site. As shown in FIG. 36, wing contact region 2214 can be adhered to the first top surface region of the wedge-shaped portion 3502. The strip 2200 can then be looped around the securing device 3502 and the wings 102 of the needle. Intermediate region 2210 can be in contact with the bottom surface of the wedge-shaped portion 3502, between the bottom surface and the patient's skin. The top end portion 2204 can be arranged over the front-side of the wings 102 and can be adhered to the surface of the skin adjacent to the patient access site as shown. When attached to the needle 100 and the securing device 3502, the arrangement of the top end region 2204 and the wing contact region 2214 of each strip 2200 prevents needle 100 from withdrawing from the patient access site. Moreover, since the securing device 3500 is separate from the needle 100, the bandage strips 2200 can be attached to the securing device 3500 before being applied to a needle inserted into the access. After insertion of the needle 100 into a patient access site, the securing device 3502 can be put into place and secured using the bandage strips 2200.

Figure 38:
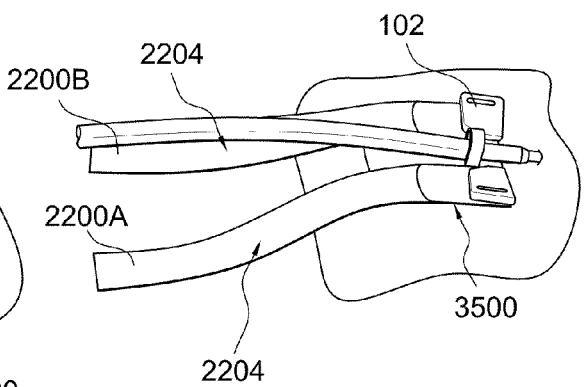
Figure 39:
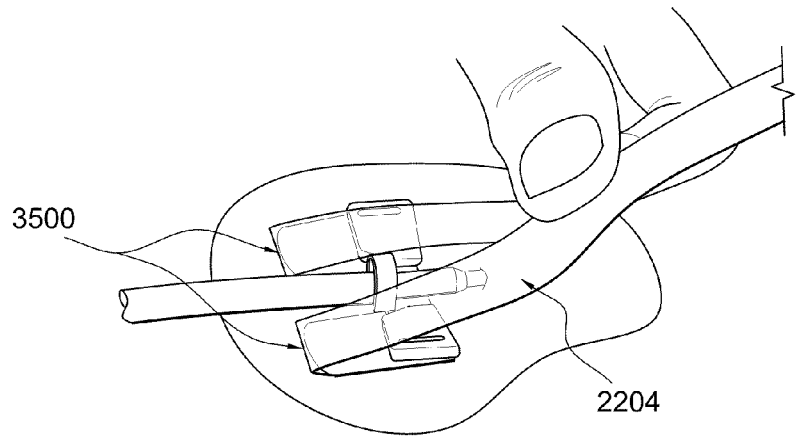
Figure 40:
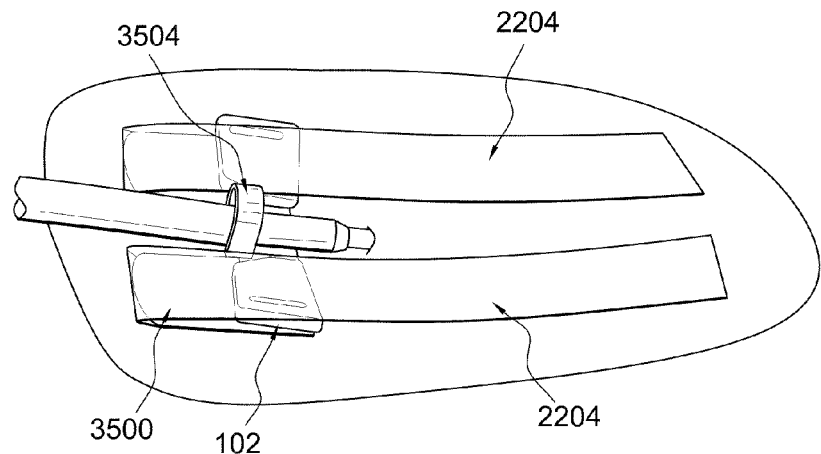

At least the wing contact region 2214 of each strip 2200 can be attached to the first top surface region of the wedge-shaped portion 3502. The intermediate region 2210 may also be attached to the bottom surface of the wedge-shaped portion 3502. After insertion of the needle 100 into the access site, the wedge-shaped portion 3502 with pre-assembled strips 2200 can be moved into place adjacent the wings 102 of the needle, as shown in FIG. 38. Referring to FIGS. 39-40, each strip 2200 can loop around the wedge-shaped portion and over the front-side of the wings 102 with the intermediate region 2210 in contact with the bottom surface of the wedge-shaped portion 3502. The top end region 2204 of each strip 2200 can be attached to the skin 402 of the patient and can hold the needle-securing device assembly in place with the needle 100 inserted into the patient access site 406, as shown in FIG. 40.

Figure 41:
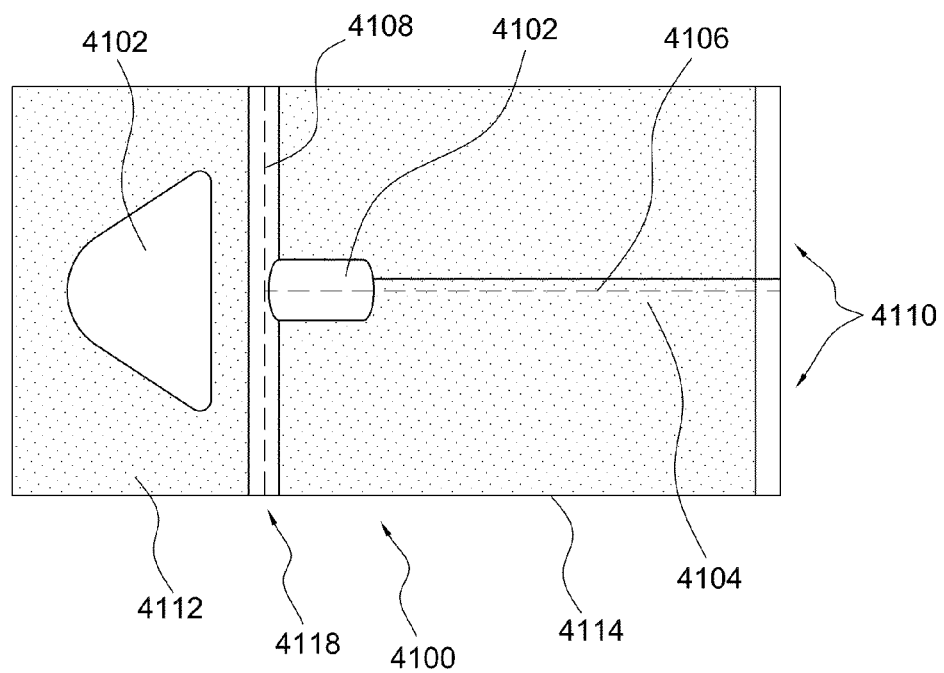
FIG. 41 shows a bandage having a viewing window, according to one or more embodiments of the disclosed subject matter.
Figure 42:
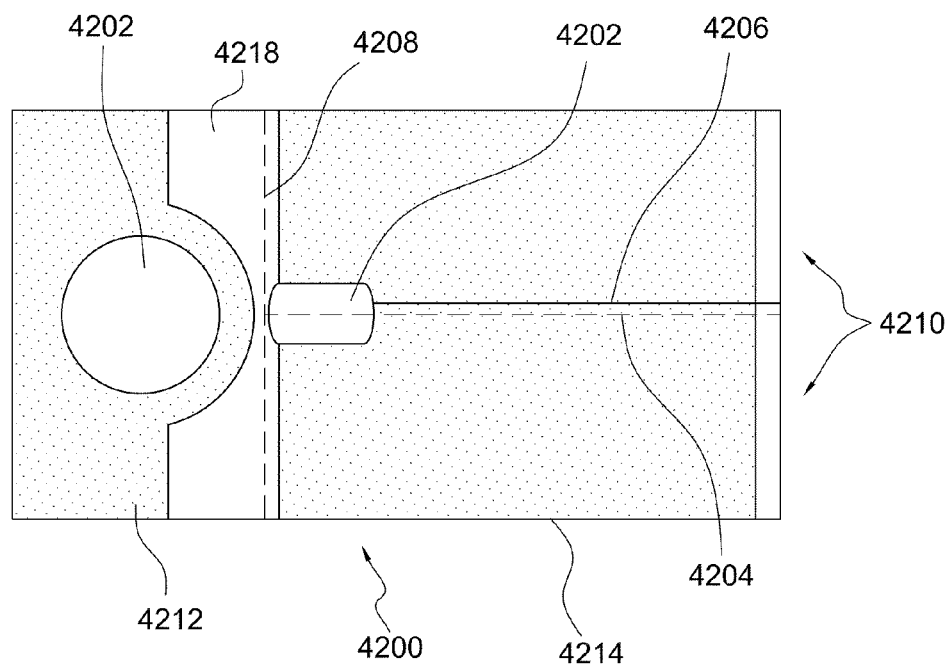
FIG. 42 shows another bandage having a viewing window, according to one or more embodiments of the disclosed subject matter.

Referring to FIG. 41, a bandage 4100 for use in securing a needle to a patient access site and/or promoting clotting of the patient access site after needle removal is shown. The bandage 4100 can include a first region 4112 having a first adhesive thereon and a second region 4114 having a second adhesive thereon. The first and second adhesives may be the same. Both the first and second adhesive may be any adhesive that is commonly used in bandage applications, such as Tegaderm™ (available through 3M™). Within the first region 4112 can be a viewing window 4102. The viewing window 4102 can be sized and shaped to provide a view of the region surrounding a needle insertion point. The window can have a tapered shape as shown in FIG. 41, a circular or elliptical shape as shown in FIG. 42, or any other shape capable of providing a view of the needle insertion point underneath the bandage. The viewing window (and even the entire bandage) may be formed from a material that is transparent or at least substantially translucent so as to permit adequate inspection of the underlying needle insertion point. The viewing window 4102 can be positioned such that a person can view the patient access site with the needle therein when the bandage is placed over the patient access site. In particular, the viewing window 4102 can be provided without an adhesive. After removal of the needle, finger pressure can be applied to the viewing window 4102 and thereby to the patient access site to encourage clotting.

The second region 4114 can include a hole 4102 that allows a portion of the needle body to pass therethrough. The hole 4102 can be arranged such that the second region 4114 is attached to only a portion of the needle hub when the needle is inserted into the patient access site and the viewing window 4102 of the first region 4112 is aligned with the patient access site. For example, a portion of the adhesive in the second region 4114 may be disposed so as to adhere to only the rear half of wings of a butterfly needle (see, for example, FIG. 44). The second region 4114 can be divided into two substantially equal size tabs 4104 by a cut line extending longitudinally from the hole 4102 to an end of the bandage 4100. In use, tabs 4104 can be positioned on the patient's skin so as to have a gap therebetween (see, for example, FIG. 44). Alternatively, hole 4102 can be extended to the end of the bandage 4100, thereby producing a pair of tabs 4104 with a gap therebetween. The ends 4110 of the tabs 4104 of the second region 4114 can be provided without any adhesive to assist in removal of the tabs 4104 from the patient skin after treatment.

The bandage 4100 can also be provided with one or more covers to protect the surfaces of the bandage 4100 prior to use. Such covers can be formed from paper and/or a flexible polymer. The first region 4112 can have a first cover, while each tab 4104 in the second region 4114 can have its own respective cover. Although the covers are not specifically shown in FIG. 41, the first cover is represented by the respective edges of the bandage 4100 in the first region 4112 and a first demarcation line 4108. The respective covers for the tabs 4104 are also represented by the respective edges of the bandage in the second region 4114, the first demarcation line 4108, and a second demarcation line 4106. Demarcation lines 4106, 4108 can represent cut lines such that the individual covers for the first and second regions can be formed from a single piece of material.

A third region 4118 can be provided between the first region 4112 and the second region 4118. In some embodiments, the third region 4118 can be provided without any adhesive thereon to assist in removal of the bandage 4100 from the needle and/or patient skin. In such a configuration, the third region 4118 can be protected by the one or more covers protecting the first and second regions, as reflected by the cover demarcation lines 4106, 4108. In other embodiments, third region 4118 can be provided with adhesive but with a cover separate from either the first or second regions. This cover may be removed after needle removal to expose the adhesive in the third region to assist in the hemostasis process.

The bandage 4100 can be made of a flexible material. For example, the bandage 4100 can be made of a clear polyethylene film. The polyethylene film can have a thickness of, for example, approximately 0.007 cm to 0.038 cm. The bandage can be substantially rectangular with a width between approximately 4 cm and 5 cm (e.g., 4.1 cm) and a length between approximately 6.5 cm and 8 cm (e.g., 7.6 cm). Other sizes and shapes for the bandage and the various features thereof are also possible according to one or more contemplated embodiments. In addition, the bandage may include a component to assist in applying pressure to the access site after needle removal. For example, the viewing window may include a bubble-shaped protrusion, such as an air-filled bubble portion, for applying pressure to the access site. Alternatively, the bubble portion can be provided separate from the bandage, for example, on a separate piece of tape applied over the viewing window after needle removal to apply pressure to the bleeding access site.

Another embodiment of a bandage 4200 is shown in FIG. 42. Bandage 4200 is similar to bandage 4100 in that it includes a viewing window 4202, a first region 4212, a second region 4214, a hole 4202, tabs defined by cutline 4206, and a third region 4218. As with bandage 4100, demarcation lines 4204, 4208 can represent cut lines for forming individual covers for each region of the bandage 4200. In contrast to bandage 4100, viewing window 4202 can be substantially circular. The adhesive in the first region 4212 can be arranged to follow a back edge of the viewing window 4202. In addition, the size of the third region 4218 is expanded as compared to that of bandage 4100. The expanded third region 4218 can be arranged to coincide with a portion of the needle structure, e.g., the front portion of wings of the needle. This may facilitate needle removal since only a smaller portion of the wings of the needle are connected to the bandage.

Figure 43:
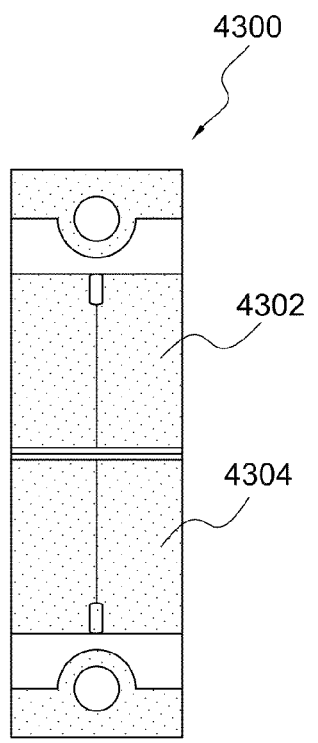
FIG. 43 shows a pair of bandages packaged together, according to one or more embodiments of the disclosed subject matter.

One or more bandages 4200 (or any of the other bandages disclosed herein) can be fabricated from a single piece of rectangular material. For example, a pair of bandages can be formed from a single piece of material 4300, as shown in FIG. 43. The piece of material can be, for example, between 4 cm and 5 cm in width and between 13 and 16 cm in length. A first bandage 4302 can be formed from a first half of the material by applying adhesive and introducing cuts/holes at appropriate portions thereof. A second bandage 4304 can be similarly formed from the second half of the material 4300. A perforation can be introduced between the first bandage 4302 and the second bandage 4304 to allow a user to separate the first and second bandages prior to use. The first and second bandages formed on the single piece of material can be part of a kit, for example, with a twin-pack of needles for use by a patient.

Figure 44:
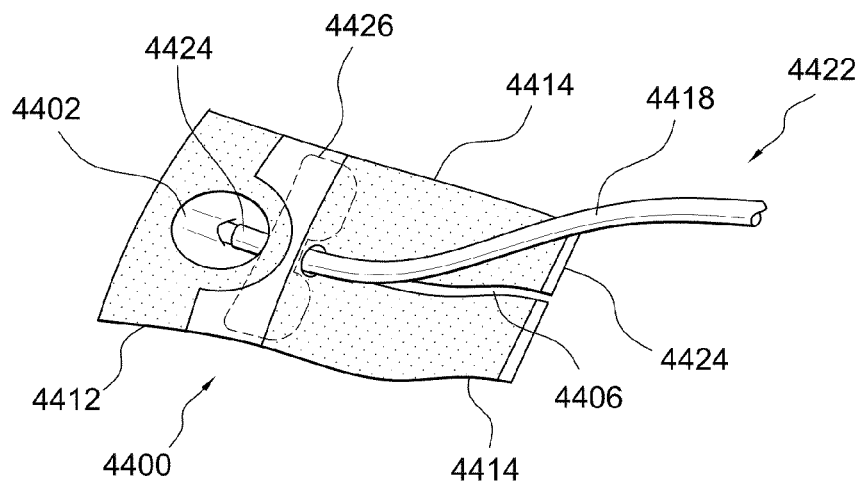
FIG. 44 shows the bandage of FIG. 41 applied to a butterfly needle inserted into a patient access, according to one or more embodiments of the disclosed subject matter.

Referring to FIG. 44, a bandage 4400 is shown applied to a patient access site with a needle 4424 inserted therein. Bandage 4400 is substantially similar to the bandage 4200 shown in FIG. 42. Viewing window 4402 of the first region 4412 can be arranged over the patient access site so as to allow inspection thereof while the needle 4424 is inserted into the site. Tubing 4418 extends rearward from a hub of the needle through a hole in the second region 4414 of the bandage 4400. The tabs of the second region 4414, defined by cut line 4406, can be adhered to the patient's skin and rear portions of the wings 4426 of the needle 4424. The wings 4426 are thereby held against the patient's skin preventing movement of the needle 4424 away from the patient access site. The third region, arranged between the first region 4412 and the second region 4414 of the bandage 4400, can be adhesive-less.

When treatment is complete, the second region 4414 can be peeled from the skin using tabs 4424. As the second region 4414 is pulled away from the skin, the adhesive of the bandage in the first and second regions can also be pulled away from the wings 4426 of the needle 4424, thereby allowing the needle to be removed from the patient access site. At least a portion of the first region 4412 can remain attached to the patient's skin during needle removal such that the bandage remains aligned with the patient access site. After needle removal, the adhesive region surrounding the viewing window 4402 in the first region 4412 can be pressed down to adhere to the patient's skin and form a barrier around the access site. Finger pressure can be applied to access site through the viewing window 4402 during and/or after needle removal to encourage clotting.

Figure 45:
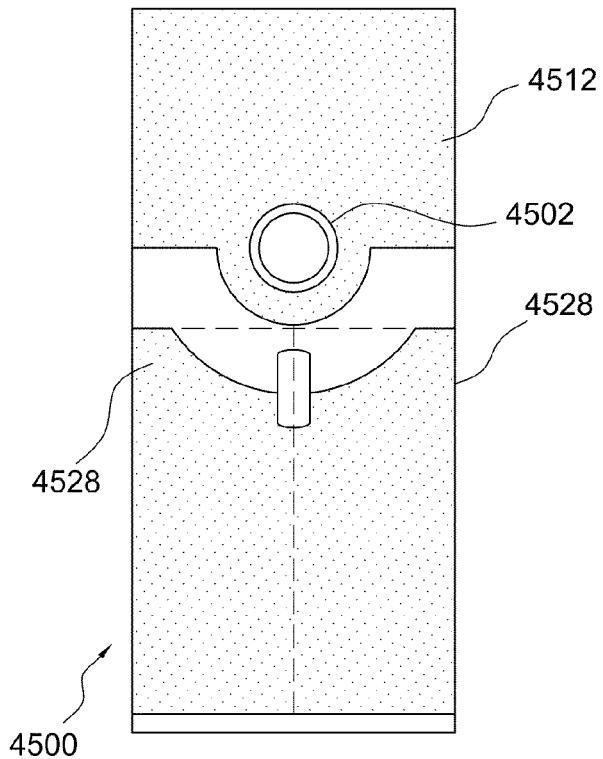
FIG. 45 shows another bandage having a viewing window with a target, according to one or more embodiments of the disclosed subject matter.

Another embodiment of a bandage 4500 is shown in FIG. 45. Bandage 4500 is similar to bandage 4200 of FIG. 42. In contrast to bandage 4200, the shape and position of the third region (between first region 4512 and tabs 4528 of the second region) is such that a smaller portion of the needle wings are attached to the bandage 4500 to provide more convenient needle removal. In addition, the viewing window can be provided with a marking or target 4502 to assist in the positioning of the viewing window over the patient access site. For example, the target 4502 can be arranged to account for potential misalignment due to a skewed viewing angle.

Figure 46:
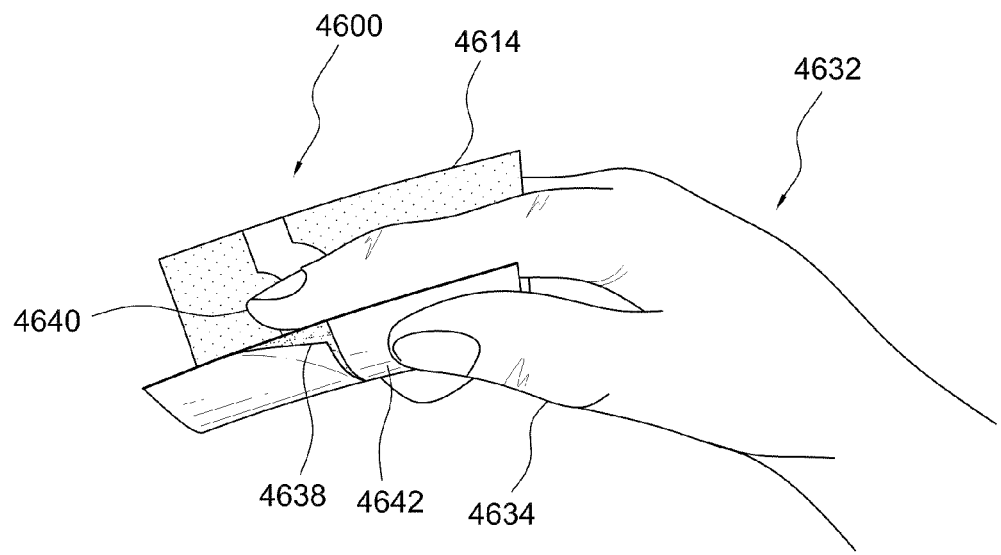
FIG. 46 shows an aspect of one-handed application of the bandage of FIG. 45, according to one or more embodiments of the disclosed subject matter.

The bandages and needle systems disclosed herein have particular application to patients who may be self-cannulating, for example, to undergo home dialysis treatments. Accordingly, aspects of the disclosed bandages and needle systems may allow for single-handed operation such that a patient can insert a needle into an access on one arm using the opposite hand without assistance from someone else. Referring to FIG. 46, a bandage 4600 can be held by a single hand 4632 for application to the skin of a patient. The structure of bandage 4600 can be substantially similar to that of bandage 4500 shown in FIG. 45. The patient may hold the bandage 4600 using thumb 4634, index finger 4640, and/or middle finger (not shown) so as to curl the bandage 4600 into a U-shape. The curling may allow for easy removal of cover 4638 of the first region by the other hand of the patient while cover 4642 of the second region remains in place.

The bandage 4600 can be applied using a single-hand 4632 by lightly dragging the first region over the skin until the viewing window 4625 lines up with the needle entry of the patient access. Once the viewing window 4625 is aligned, the first region may be adhered to the skin by pressing down on the various parts of the first region using the middle finger and thumb of hand 4632. The tabs 4614 of the second region can be positioned by hand 4632 around the tubing 4618 connected to needle 4624 such that the tubing 4618 passes through the hole of the second region. Hand 4632 can then remove the second cover 4642 to expose the adhesive of the second region. The tabs 4614 of the second region can be applied to the skin using hand 4632 to thereby secure the needle 4624 in place in the patient access. Note that the shape of the second and third regions can be such that only an outer edge portion 4634 of the needle wings 4626 are adhered to bandage 4600. The needle 4624 can thus be retained in place while allowing for easy one-handed removal of the needle when treatment is finished.

Figure 47:
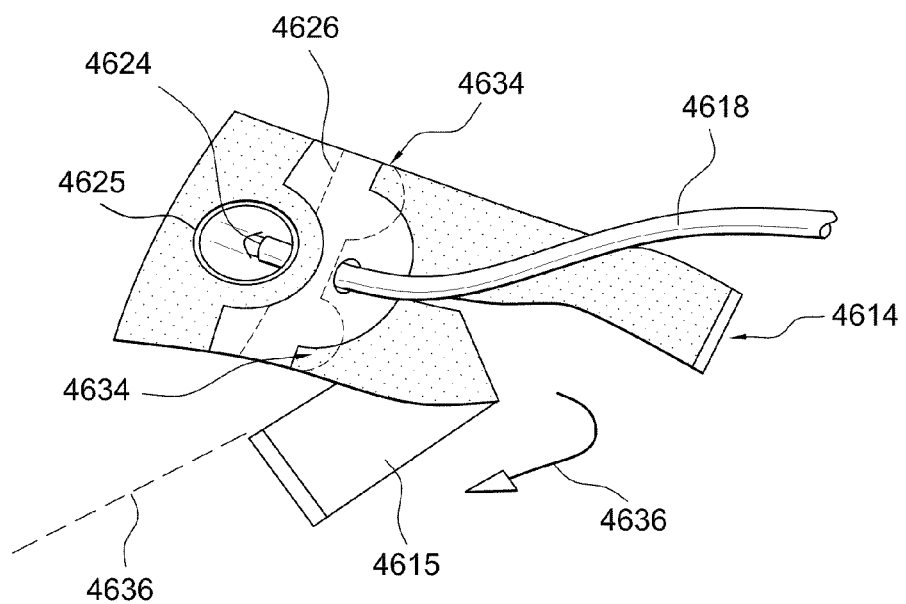
FIG. 47 shows the bandage of FIG. 45 applied to a butterfly needle inserted into a patient access during a first step of a needle removal process, according to one or more embodiments of the disclosed subject matter.
Figure 48:
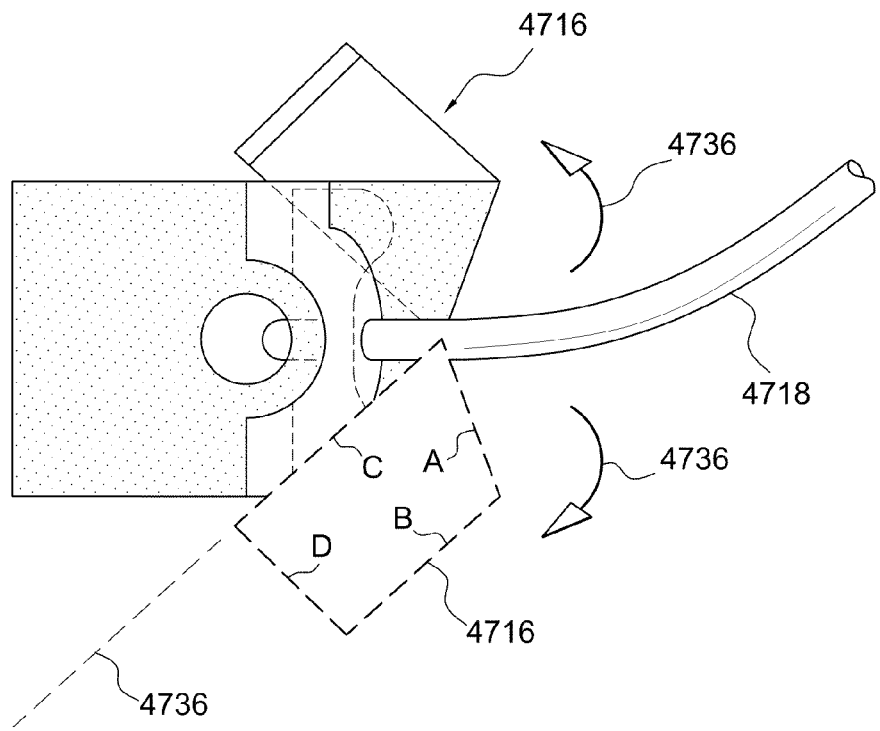
FIG. 48 shows a top view of the bandage of FIG. 45 applied to a butterfly needle inserted into a patient access during a second step of a needle removal process, according to one or more embodiments of the disclosed subject matter.

To allow removal of the needle 4624 from the patient access site, the bandage can be manipulated by hand 4632. Referring to FIGS. 47-48, a first step in the bandage manipulation for needle removal is shown. In particular, each of the tabs 4614 of the second region can be removed from the patient's skin and folded under along direction 4636 so as to stick to itself, resulting in angled tab portions 4716. In other words, each tab is folded along edge A, which is angled with respect to the longitudinal axis of the tab such that edges B and C and parallel to direction 4736. The folded tab can thus be attached to itself with upturned adhesive portions 4615 remaining exposed. As shown in FIG. 48, the adhesive portion of the bandage can remain connected to the portion of the wings 4634.

Figure 49:
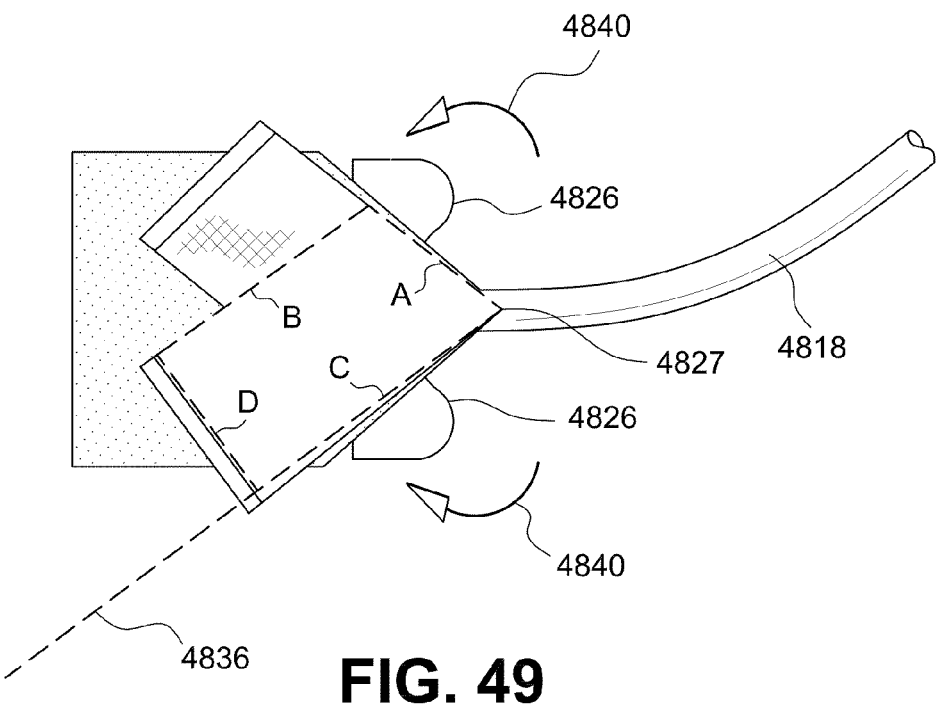
FIG. 49 shows a top view of the bandage of FIG. 45 applied to a butterfly needle inserted into a patient access during a third step of a needle removal process, according to one or more embodiments of the disclosed subject matter.

Referring to FIG. 49, each tab can again be folded back on itself, this time along direction 4840. In other words, each tab can be folded along edge C such that the exposed portions 4615 are adhered to the top surface of the bandage 4600. Wings 4826 are thus detached from adhesive in the second region of the bandage 4600. Hand 4632 can then remove needle from the access site. For example, hand 4632 can press down on the top surface of the folded tabs 4827 directly over the viewing window using the index finger while the thumb and the middle finger of hand 4632 can be used to remove the needle from the access site.

To assist the patient and/or user in the manipulation of the bandage to allow needle removal, the tabs can include printed lines to indicate where the tab should be folded. In addition, the tabs can include a target (not shown) corresponding to the location of the viewing window when the tabs are in the folded configuration of FIG. 49. The patient/user can press on the labeled target to apply pressure to the needle access even though the viewing window may be covered and otherwise obscured. After removing the needle, the thumb and middle finger of hand 4632 can push down on the regions of the first region surrounding the viewing window into contact with the patient's skin. The index finger of hand 4632 can continue to apply pressure to the patient access site until hemostasis occurs. The bandage can be maintained on the skin for a period of time to protect the wound after clotting. When desired, the bandage can be removed without affecting the scab of the wound since the viewing window in contact with the scab does not have any gauze or cotton.

Features of the disclosed embodiments may be combined, rearranged, omitted, etc., within the scope of the present disclosure to produce additional embodiments. Furthermore, certain features may sometimes be used to advantage without a corresponding use of other features.

It is, thus, apparent that there is provided, in accordance with the present disclosure, safe needle and bandage methods, apparatus, and systems. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A bandage for securing a butterfly needle to a patient access site, the needle having a pair of wings extending radially from the hub of the needle, the bandage comprising:
   a flexible material having:
      a first region with a first adhesive on at least a surface portion thereof;
      a second region with a gap therein so as to form a pair of tabs separated by said gap, at least an end portion of each of the tabs being free from adhesive; and
      a third region arranged between the first and second regions, the third region having a second adhesive on at least a surface portion thereof; and
   a hemostasis pad arranged in said first region, the hemostasis pad being constructed to promote clotting of blood that contacts said pad,
   wherein the third region is arranged so as to contact the pair of wings of the butterfly needle for releasably coupling the bandage thereto, and
   the hemostasis pad is arranged so as to contact the patient access site when the third region is coupled to the butterfly needle inserted into the patient access site.

2. The bandage of claim 1, wherein the first region is arranged so as to releasably couple the bandage to the skin of the patient when the third region is coupled to the butterfly needle inserted into the patient access site.

3. The bandage of claim 1, wherein said second region tabs are completely free from adhesive.

4. The bandage of claim 1, wherein the hemostasis pad includes a gel with clot promoting material.

5. The bandage of claim 1, wherein the hemostasis pad includes gauze with clot promoting material.

6. The bandage of claim 1, wherein the first adhesive is configured for contact with and to adhere to a patient's skin.

7. The bandage of claim 1, wherein the second adhesive is configured for contact with and to adhere to the pair of wings of the butterfly needle.

8. The bandage of claim 1, wherein said flexible material is a plastic material.

9. The bandage of claim 1, wherein said flexible material is a transparent material.

10. The bandage of claim 1, further comprising a hemostasis pad cover, which includes a portion that covers the hemostasis pad during insertion and use of the butterfly needle.

11. The bandage of claim 10, wherein the hemostasis pad cover includes a T-shaped portion for attaching the cover to tubing of the butterfly needle by wrapping around a circumference thereof, and the hemostasis pad cover is arranged such that the portion that covers the hemostasis pad is removed as the needle is removed from the patient access, thereby exposing the hemostasis pad to blood from the patient access.

12. The bandage of claim 10, wherein the hemostasis pad cover includes an adhesive for attaching the cover to tubing of the butterfly needle, and the hemostasis pad cover is arranged such that the portion that covers the hemostasis pad is removed as the needle is removed from the patient access, thereby exposing the hemostasis pad to blood from the patient access.

13. A needle assembly comprising:
   a butterfly needle having a tip, a hub with a pair of wings extending radially therefrom, and tubing extending from the hub and in fluid communication with the tip; and
   a bandage for securing the butterfly needle to a patient access site when the needle is inserted therein, the bandage having:

a first end region with a first adhesive on at least a portion thereof and a hemostasis pad;
a second end region without any adhesive;
a middle region arranged between the first and second end regions, the middle region being releasably connected to the pair of wings by a second adhesive on at least a portion of the middle region; and
wherein the first end region is arranged for contact with the patient's skin with the hemostasis pad adjacent to a patient access site when the butterfly needle is inserted into the patient access site.

14. The needle assembly of claim 13, wherein the second end and middle regions are arranged such that the middle region can be disconnected from the pair of wings when the butterfly needle in inserted into the patient access site by pulling on said second end region.

15. The needle assembly of claim 13, wherein the bandage is configured such that the first end region remains connected to the patient's skin with the hemostasis pad adjacent to the patient access site when the butterfly needle is removed from the patient access site.

16. The needle assembly of claim 13, wherein the butterfly needle is only connected to the bandage in said middle region.

17. The needle assembly of claim 13, further comprising a needle guard movably coupled to said tubing, the needle guard having a locking portion, wherein the tip of said butterfly needle is fully contained within the needle guard when the wings of the needle are moved into said locking portion.

18. The needle assembly of claim 17, wherein the needle guard includes a finger guard arranged such that pressure can be applied to the patient access site by pressing on the finger guard during removal of the butterfly needle from the patient access site.

19. The needle assembly of claim 18, wherein the finger guard is releasably attached to the needle guard.

20. The needle assembly of claim 18, wherein the finger guard is releasably attached to the needle guard by a piece of tape.

* * * * *